United States Patent [19]
Yamamoto et al.

[11] Patent Number: 5,304,556
[45] Date of Patent: Apr. 19, 1994

[54] BENZA-TRIAZINONE DERIVATIVES

[75] Inventors: Akihiro Yamamoto; Shuji Morita, both of Yokohama; Yoshio Hayashi, Ushiku; Noboru Yamada, Yamato; Toshihito Kitamura, Yokohama, all of Japan

[73] Assignee: Mitsubishi Kasei Corporation, Tokyo, Japan

[21] Appl. No.: 993,044

[22] Filed: Dec. 18, 1992

[30] Foreign Application Priority Data

Dec. 25, 1991 [JP] Japan .................. 3-343687
Nov. 16, 1992 [JP] Japan .................. 4-305574

[51] Int. Cl.$^5$ .................. A61K 31/53; C07D 253/10
[52] U.S. Cl. .................. 514/243; 514/252; 514/259; 514/309; 514/414; 544/183; 544/237; 544/284; 544/287; 546/141; 548/472; 548/473
[58] Field of Search .................. 544/183; 514/243

[56] References Cited

U.S. PATENT DOCUMENTS 4,619,941 10/1986 Wright et al. .................. 514/397
4,680,293 7/1987 Wright, Jr. et al. .................. 544/183

FOREIGN PATENT DOCUMENTS 0145078 6/1985 European Pat. Off. .
0229391 7/1987 European Pat. Off. .
0268242 5/1988 European Pat. Off. .
0293500 12/1988 European Pat. Off. .
60-132928 7/1985 Japan .
61-176591 8/1986 Japan .
63-316778 12/1988 Japan .
1-156982 6/1989 Japan .
2-256682 10/1990 Japan .

OTHER PUBLICATIONS

Braquet et al., "Pharmacological Reviews" 39(2), 97–145 (1987).
Nakashima et al., "Saishin-Igaku" 45(3) 462–473 (1990).
"Gendai-Kagaku", Supplement 17, 207–226, 1989.

*Primary Examiner*—Mukund J. Shah
*Assistant Examiner*—Y. N. Gupta
*Attorney, Agent, or Firm*—Wenderoth, Lind & Ponack

[57] ABSTRACT

Benzamide derivatives of the following formula (I)

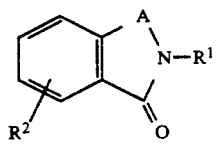

(I)

[wherein
$R^1$:

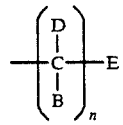

B, D: hydrogen atom, etc.
E: pyridyl group, etc.
n: integer from 0 to 2
$R^2$: $R^3R^4N$— etc.
($R^3,R^4$: optionally substituted $C_6$–$C_{14}$ aryl group, etc.)
A;

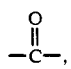

—$CH_2$—, —N=N—, —CH=N—, —N=CH—, —CH=CH— or —$CH_2$—$CH_2$—].

Optical antipodes thereof or pharmaceutically acceptable salts thereof, show excellent PAF antagonism and are effective for therapy and prophylaxis of diseases caused by PAF (bronchial asthma, nephritis, shocks, cardiac infarction, cerebral hemorrhage, ulcer, DIC, autoimmune diseases, thrombosis, etc.).

8 Claims, No Drawings

BENZA-TRIAZINONE DERIVATIVES

The present invention relates to novel benzamide derivatives and pharmacologically acceptable salts thereof. More particularly, this invention is directed to the benzamide derivatives and pharmacologically acceptable salts thereof exhibiting an antagonistic activity to a platelet activating factor.

The platelet activating factor (hereinafter referred to as "PAF"), 1-O-hexadecyl or octadecyl-2-acetyl-sn-glyceryl-3-phosphorylcholine, was found to be a factor potently aggregating platelets by Benveniste et al. in 1972, and its chemical structure was determined by Hanahan et al. in 1980. Pharmacological activity and physiological activity of PAF have recently been elucidated, and its relation with various diseases such as inflammatory diseases, allergic diseases, anaphylactic shock, DIC, asthma, ulcer of digestive organs, nephritis and the like has been clarified [Saishin Igaku, Vol. 45, p.427, 1990 (Saishin Igaku-sha); Gendai Kagaku, Supplementary Edition 17, Platelet Activating Factor (Tokyo Kagaku Dojin), etc.]. Under these circumstances, search for compounds exhibiting PAF antagonism has been advanced.

A lot of thienotriazolo-1,4-diazepine compounds showing PAF antagonism have been disclosed, for example, in Japanese Patent Publication (Kokai) Sho 61-176591, Japanese Patent Publication (Kokai) Hei 1-156982. Japanese Patent Publication (Kokai) Hei 2-256682, etc. Further, various other compounds have been proposed as PAF antagonist [Braquet et al., Pharmacological Reviews, Vol. 39 (1987), p.97], but no compounds have been clinically used so far.

Japanese Patent Publication (Kokai) Sho 63-316778 describes in Table 1 that the compound of the following formula (A):

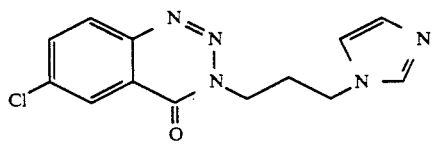

inhibits thromboxane synthetase enzyme.

Japanese Patent Publication (Kokai) Sho 60-132928 describes in Table 2 that the compound of the following formula:

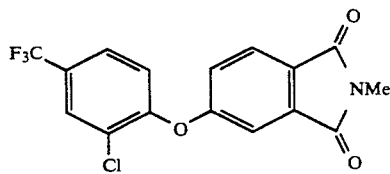

shows herbicidal activity.

However, these two publications give no suggestion that the above compounds are useful as PAF antagonist.

As the result of extensive investigations for providing novel compounds exhibiting PAF antagonism, the present inventors have found that particular benzamide derivatives have excellent physiological activity, and they are useful as PAF antagonist.

Accordingly, the present invention provides benzamide derivatives of the following formula (I):

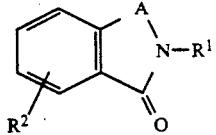

[in the above formula (I), R: represents a group of the following formula (II):

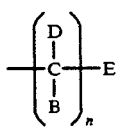

(in the above formula (II), n represents an integer from 0 to 2, B and D each independently represent hydrogen atom or $C_1$-$C_4$ alkyl group, E represents a 5–6 membered heterocyclic group containing one or more hetero atoms selected from nitrogen atom, oxygen atom and sulfur atom, and said heterocyclic group optionally has one or more substituents selected from $C_1$-$C_4$ alkyl group and $C_1$-$C_4$ alkoxy group), $R^2$ represents $C_6$-$C_{12}$ aryl group, $C_6$-$C_{12}$ aryloxy group, $C_6$-$C_{12}$ arylthio group, benzyloxy group or $C_7$-$C_{13}$ arylcarbonyl group, said groups each optionally having a substituent, or a group of the following formula (III):

$$R^3R^4N— \quad (III)$$

(in the above formula (III), $R^3$ represents $C_6$-$C_{12}$ aryl group optionally having a substituent, $R_4$ represents $C_6$-$C_{12}$ aryl group, hydrogen atom, $C_1$-$C_4$ alkyl group or $C_3$-$C_8$ cycloalkyl group), or a group of the following formula (IV):

$$R^5R^6CH— \quad (IV)$$

(in the above formula (IV), $R^5$ represents $C_6$-$C_{12}$ aryl group optionally having a substituent, $R^6$ represents $C_6$-$C_{12}$ aryl group optionally having a substituent, hydrogen atom, $C_1$-$C_4$ alkyl group or $C_3$-$C_8$ cycloalkyl group), and A represents

—CH$_2$—, —N=N—, —CH=N—, —N=CH—, —CH=CH—, or —CH$_2$—CH$_2$—], optical antipodes thereof, or pharmacologically acceptable salts thereof, and a prophylactic or therapeutic pharmaceutical composition for diseases caused by PAF, said composition containing the above compound as an active ingredient. The present invention will be explained in more detail below.

The subject matter of the present invention includes a benzamide derivative of the following formula (I):

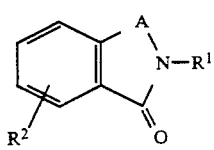

{in the above formula (I), $R^1$ represents a group of the following formula (II):

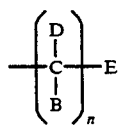

(II)

(in the above formula (II), n represents an integer from 0 to 2, B and D each independently represent hydrogen atom or $C_1$-$C_4$ alkyl group (e.g. methyl group, butyl group, etc.), E represents a 5-6 membered heterocyclic group containing one or more hetero atoms selected from nitrogen atom, oxygen atom and sulfur atom (e.g. thienyl group, furyl group, imidazolyl group, pyrazolyl group, pyridyl group, N-oxypyridyl group, pyrimidyl group, etc.), and said heterocyclic group optionally having one or more substituents selected from the group consisting of $C_1$-$C_4$ alkyl group (e.g. methyl group, butyl group, etc.) and $C_1$-$C_4$ alkoxy group (e.g. methoxy group, butoxy group, etc.)]. $R^2$ represents $C_6$-$C_{12}$ aryl group (e.g. phenyl group, xylyl group, naphthyl group, etc.), $C_6$-$C_{12}$ aryloxy group (e.g. phenoxy group, xylyloxy group, naphthyloxy group, etc.), $C_6$-$C_{12}$ arylthio group (e.g. phenylthio group, xylylthio group, napthylthio group, etc.), benzyloxy group or $C_7$-$C_{13}$ arylcarbonyl group (e.g. benzoyl group, xylylcarbonyl group, naphthoyl group, etc.), said groups each optionally having one or more substituents selected from the group consisting of $C_1$-$C_4$ alkyl group (e.g. methyl group, butyl group etc.), $C_3$-$C_8$ cycloalkyl group (e.g. cyclopropyl group, cyclopentyl group, cyclooctyl group, etc.), $C_1$-$C_4$ alkoxy group (e.g. methoxy group, butoxy group, etc ), $C_2$-$C_4$ alkenyl group (e.g. vinyl group, butenyl group, etc.), $C_2$- $C_4$ alkynyl group (e.g. ethynyl group, butynyl group, etc.), $C_3$-$C_4$ alkenyloxy group (e.g. allyloxy group, butenyloxy group, etc.), $C_3$-$C_4$ alkynyloxy group (e.g. propynyloxy group, butynyloxy group, etc.), hydroxyl group, halogen atom (e.g. fluorine atom, chlorine atom, bromine atom, iodine atom), amino group, $C_1$-$C_4$ alkylamino group (e.g. methylamino group, butylamino group, etc.), $C_2$-$C_6$ dialkylamino group (e.g. dimethylamino group, methylethylamino group, diethylamino group, etc.), trifluoromethyl group, cyano group, nitro group, $C_1$-$C_4$ hydroxyalkyl group (e.g. hydroxymethyl group, hydroxybutyl group, etc.), $C_1$-$C_4$ aminoalkyl group (e.g. aminomethyl group, aminobutyl group, etc.), $C_1$-$C_4$ cyanoalkyl group (e.g. cyanomethyl group, cyanobutyl group), —$COOR^7$, —$COR^7$, —$SO_2R^7$, —$NHCOOR^7$, —$NR^8COR^{10}$, —$CONR^8R^{10}$, —$OCONR^8R^9$, —$NR^8CONR^9R^{10}$ and —$CONR^8COR^9$ [which $R^7$ and $R^9$ each independently represent $C_1$-$C_4$ alkyl group (e.g. methyl group, butyl group, etc.) or $C_3$-$C_8$ cycloalkyl group (e.g. cyclopropyl group, cyclopentyl group, cyclooctyl group, etc.), $R^8$ and $R^{10}$ each independently represent hydrogen atom, $C_1$-$C_4$ alkyl group (e.g. methyl group, butyl group, etc.) or $C_3$-$C_8$ cycloalkyl group (e.g. cyclopropyl group, cyclopentyl group, cyclooctyl group, etc.)], a group of the following formula (III):

$R^3R^4N—$ (III)

[in the above formula (III), $R^3$ represents $C_6$-$C_{12}$ aryl group (e.g. phenyl group, xylyl group, naphthyl group, etc.), $R^4$ represents $C_6$-$C_{12}$ aryl group (e.g. phenyl group, xylyl group, naphthyl group, etc.), hydrogen atom, $C_1$-$C_4$ alkyl group (e.g. methyl group, butyl group, etc.) or $C_3$-$C_8$ cycloalkyl group (e.g. cyclopropyl group, cyclopentyl group, cyclooctyl group, etc.), and the aryl group defined by $R^3$ and $R^4$ optionally has one or more substituents selected from the same group as defined above in connection with the substituent for $R^2$]or a group of the following formula (IV):

$R^5R^6CH—$ (IV)

[in the above formula (IV), $R^5$ represents $C_4$-$C_{12}$ aryl group (e.g. phenyl group, xylyl group, naphthyl group, etc.), $R^4$ represents $C_6$—$C_{12}$ aryl group (e.g. phenyl group, xylyl group, naphthyl group, etc.), hydrogen atom, $C_1$-$C_4$ alkyl group (e.g. methyl group, butyl group, etc.), or $C_3$-$C_8$ cycloalkyl group (e.g. cyclopropyl group, cyclopentyl group, cyclooctyl group, etc.), and the aryl group defined by $R^5$ and $R^6$ optionally has one or more substituents selected from the same group as defined in said $R^2$], and A represents

—$CH_2$—, —$N=N$—, —$CH=N$—, —$N=CH$—, —$CH=CH$— or —$CH_2CH_2$—}, optical antipodes thereof, and pharmacologically acceptable salts thereof.

Preferred are those compounds which are represented by the above formula (I), wherein n is an integer of 1, and B and D are each hydrogen atom, E is pyridyl group or N-oxypyridyl group, A is

—$N=N$—, or —$CH_2$—$CH$— in the formula (II).

More preferred are those compounds which are represented by the above formula (I), wherein $R^2$ is aryloxy group optionally substituted by a substituent or a group of the formula (III):

$R^3R^4N—$ (III)

[in the above formula (III), $R^3$ is optionally substituted $C_6$-$C_{12}$ aryl group and $R^4$ is optionally substituted $C_6$-$C_{12}$ aryl group, hydrogen atom, $C_1$-$C_4$ alkyl group or $C_3$-$C_8$ cycloalkyl group].

Examples of one or more preferable substituents which may exist on the aryl group defined by $R^2$, $R^3$, $R^4$, $R^5$ and $R^6$ are selected from the group consisting of $C_1$-$C_4$ alkyl group, $C_1$-$C_4$ alkoxy group, $C_3$-$C_4$ alkynyloxy group, hydroxy group, halogen atom, trifluoromethyl group, cyano group, nitro group, $C_1$-$C_4$ hydroxyalkyl group, —$COOR^7$, —$COR^7$, —$SO_2R^7$ and —$CONR^8R^{10}$ (in which $R^7$ is $C_1$-$C_4$ alkyl group, and $R^8$ and $R^{10}$ are each hydrogen atom or $C_1$-$C_4$ alkyl group).

Particularly preferred are the compounds which are represented by the above formula (I), wherein $R^1$ is a group of the following formula:

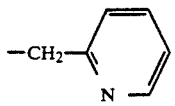

$R^2$ is a group of the following formula (III):

$$R^3R^4N- \quad (III)$$

(in the above formula (III), $R^3$ and $R^4$ are 4-cyanophenyl group), and A is

The salts of the compounds of the above formula (I) include physiologically acceptable salts such as inorganic salts (e.g. hydrochloride, hydrobromide, hydroiodide, sulfate, phosphate, etc.) and organic salts (e.g. oxalate, maleate, fumarate, lactate, malate, citrate, tartrate, benzoate, methanesulfonate, etc.). Since the compounds of the formula (I) and salts thereof may exist in the form of hydrate or solvate, these hydrates and solvates are included in the scope of the present invention.

For example, the compounds of the present invention can be prepared according to the following processes.

Production 1

In the case of the compounds (I) wherein $R^2$ is optionally substituted phenoxy or phenylthio group, the following reaction scheme may be employed.

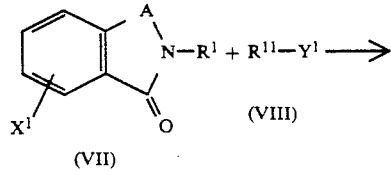

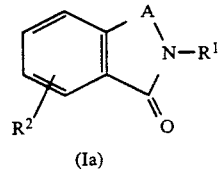

(in the above formula, $R^1$ and A are as defined above, $X^1$ represents nitro group, hydroxy group or halogen atom, $R^{11}$ represents optionally substituted phenyl group, and $Y^1$ represents hydroxy group, halogen atom, $OM^1$ or $SM^1$ (in which $M^1$ represents sodium, lithium or potassium atom, with the proviso that, when $X^1$ is nitro group, $Y^1$ represents $OM^1$ or $SM^1$, and when $X^1$ is hydroxy group, $Y^1$ represents halogen atom, and when $X^1$ is halogen atom, $Y^1$ represents hydroxy group).

Thus, the compound of the formula (Ia), one of the objective compounds, can be prepared by reacting the compound of the formula (VII) with the compound of the formula (VIII).

When $X^1$ is nitro group and $Y^1$ is $OM^1$ or $SM^1$, the reaction may be effected in an inert solvent such as dimethylformamide, dimethyl sulfoxide or the like at temperature from room temperature to 160° C., preferably 100° to 160° C.

When $X^1$ is hydroxy group and $Y^1$ is halogen atom, or when $X^1$ is halogen atom and $Y^1$ is hydroxy group, the reaction may be effected according to Ullmann reaction in the presence of a cupper catalyst such as copper dust, copper halide (I), copper halide (II), copper oxide (II) or the like, and an inorganic salt such as potassium carbonate, sodium carbonate or the like, at temperature from 100° to 200° C. in an inert solvent such as toluene, xylene, dioxane, 1,2-dichlorobenzene, dimethylformamide, dimethyl sulfoxide, N-methyl-2-pyrolidone, pyridine or the like.

In the case of the compounds (I) wherein $R^2$ is optionally substituted benzyloxy group, the following reaction scheme may be employed.

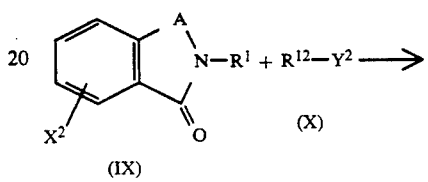

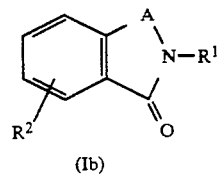

(in the above formulae, $R^1$ and A are as defined above, $X^2$ represents hydroxy group, $R^{11}$ represents benzyl group optionally substituted on the benzene ring, and $Y^2$ represents hydroxy group or halogen atom).

Thus, the compound of the above formula (Ib), one of the objective compounds, can be prepared by reacting the compound of the above formula (IX) with the compound of the above formula (X).

When $X^2$ is hydroxy group and $Y^2$ is halogen atom, the reaction may be effected in the presence of a base such as potassium carbonate, sodium carbonate, triethylamine, sodium hydroxide or the like, at temperature from 0° to 100° C. in an inert solvent such as tetrahydrofuran, dimethylformamide, dimethylsulfoxide or the like.

When $X^2$ is hydroxy group and $Y^2$ is hydroxy group, the reaction may be effected in the presence of a condensing agent such as diethylazodicarboxylate and triphenyl phosphine according to the process of Manhas et al., J. Chem. Soc., Perkin Trans. 1, (1975), p. 461.

In the case of the compounds (I) wherein $R^2$ is optionally substituted phenyl or naphthyl group, the following reaction scheme may be employed.

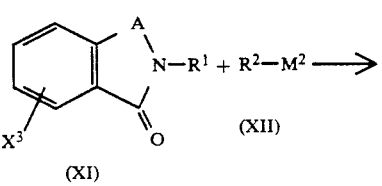

-continued

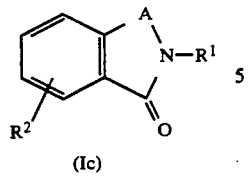
(Ic)

(in the above formulae, $R^1$ and A are as defined above, $X^3$ represents halogen atom or trifluoromethanesulfonyloxy group and $M^2$ represents Zn-hal (in which hal represents halogen atom), —Sn(CH$_3$)$_3$ or —Sn(C$_4$H$_9$)$_3$).

Thus, the compound of the above formula (Ic) can be prepared by reacting the compound of the above formula (XI) with the compound of the above formula (XII).

The above reaction is a cross-coupling reaction in the presence of a palladium or nickel catalyst according to the process of Hayashi et al., J. Am. Chem. Soc., Vol. 106 (1984), p.158; Stille et al., J. Am. Chem. Soc., Vol. 109 (1987), p.5478, and the like.

In the case of the compounds (I) wherein $R^2$ is a group of the above-identified formula (III), the following reaction schemes may be employed.

a) In the case that $R^3$ and $R^4$ are the same and represent optionally substituted phenyl group:

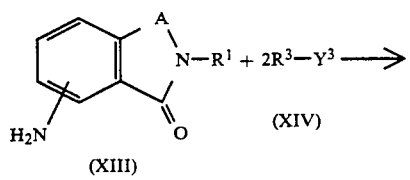
(XIII)           (XIV)

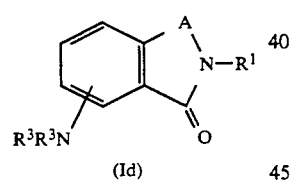
(Id)

(in the above formulae, $R^1$ and A are as defined above, and $Y^3$ represents halogen atom).

Thus, the compound of the above formula (Id), one of the present compounds, can be prepared by reacting the compound of the above formula (XIII) with 2 molar equivalents of the compound of the above formula (XIV).

The present reaction may be effected under the conditions of Ullman reaction according to Gauthier, et al., Synthesis, (1987), p. 383.

b) In the case that $R^3$ and $R^4$ are different each other:

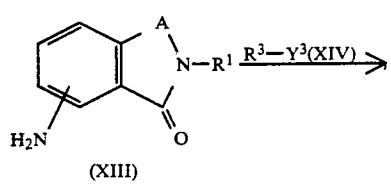
(XIII)

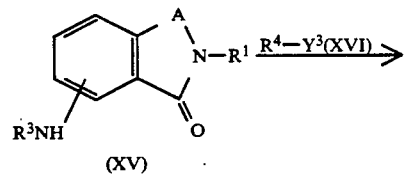
(XV)

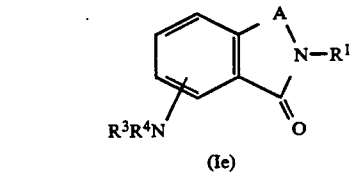
(Ie)

(in the above formulae, $R^1$ and A are as defined above, and $Y^3$ represents halogen atom).

Thus, the compound of the above formula (Ie), one of the objective compounds, can be prepared by reacting the compound of the above formula (XIII) with one molar equivalent of the compound of the above formula (XIV) under the same conditions as in the above item a), followed by reacting the resulting compound of the above formula (XV) with the compound of the above formula (XVI) under the same conditions.

The intermediates of the above formulae (VII), (IX), (XI) and (XIII) can be prepared under the following item c) or under the item of d)-g).

c) 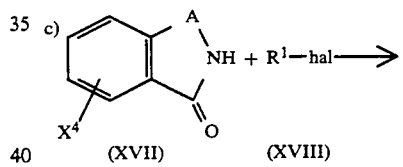
(XVII)      (XVIII)

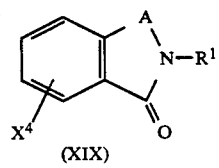
(XIX)

(in the above formulae, $X^4$ represents methoxy group, nitro group, halogen atom, or the like; $R^1$ and A are as defined above, and hal represents halogen atom).

Thus, the compound of the above formula (XIX) can be prepared by reacting the compound of the above formula (XVII) with the compound of the above formula (XVIII) in the presence of a base such as sodium hydroxide or potassium carbonate in an inert solvent such as dimethylformamide, tetrahydrofuran or the like, at temperature from 0° to 100° C., and if necessary, followed by converting $X^4$ into $X^1$, $X^2$, $X^3$ or amino group.

d) In the case that A is $$\overset{O}{\underset{}{\overset{\parallel}{-C-}}}:$$

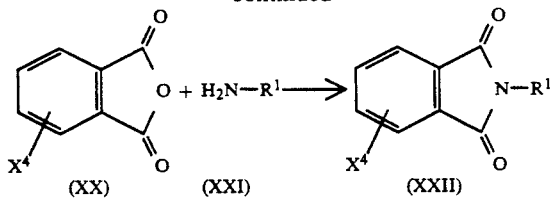

(in the above formulae, $X^4$ and $R^1$ are as defined above)

Thus, the compound of the above formula (XXII) can be prepared by reacting the compound of the above formula (XX) with the compound of the formula (XXI) in an inert solvent such as benzene, toluene or the like, or in acetic acid at temperature from 60° C. to the boiling point of the solvent used, and if necessary, followed by converting $X^4$ into $X^1$, $X^2$, $X^3$ or amino group.

e) In the case that A is —N=N—:

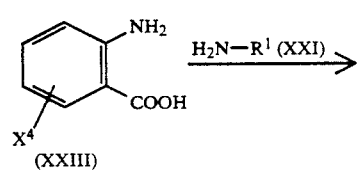

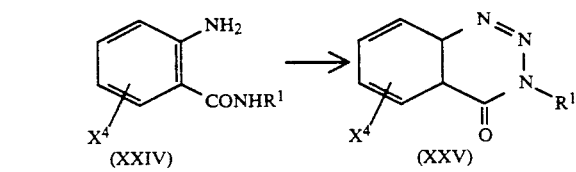

(in the above formulae, $X^4$ and $R^1$ are as defined above).

Thus, the compound of the above formula (XXV) can be prepared by reacting the compound of the above formula (XXIII) with the compound of the above formula (XXI) in the presence of a condensing agent such as diphenylphosphoryl azide or the like, to give the compound of the above formula (XXIIV) and cyclizing it according to the process of Write, Jr. et al., J. Med. Chem., Vol. 30 (1987), p.2277, and if necessary, followed by converting $X^4$ into $X^1$, $X^2$, $X^3$ or amino group in a conventional manner.

f) In the case that A is —CH₂—:

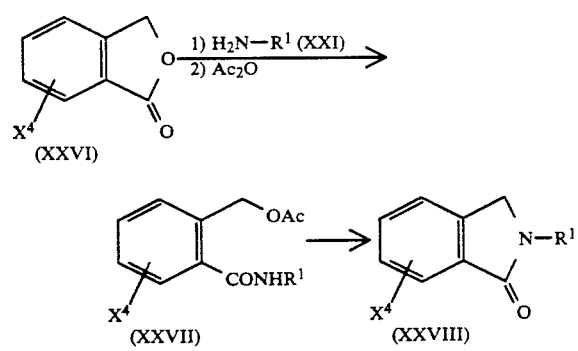

(in the above formulae, Ac represents acetyl group, and $X^4$ and $R^1$ are as defined above).

Thus, the compound of the above formula (XXVIII) can be prepared by reacting the compound of the formula (XXVI) with the compound (XXI) at about 150° C. without solvent, acetylating with acetic anhydride in a conventional manner to give the compound of the above formula (XXVII), and cyclizing it in the presence of a base such as sodium hydride in an inert solvent such as tetrahydrofuran, dimethylformamide or the like, at temperature form 0° C. to room temperature, and if necessary, followed by converting $X^4$ into $X^1$, $X^2$, $X^3$ or amino group in a conventional manner.

g) In the case that A is —N=CH—:

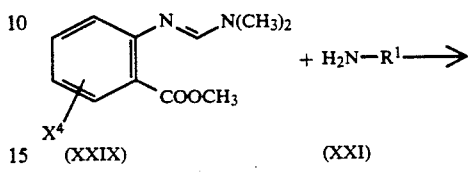

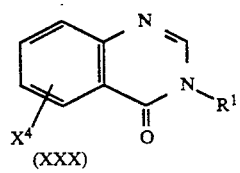

(in the above formulae, $X^4$ and $R^1$ are as defined above).

Thus, the compound of the above formula (XXX) can be prepared by reacting the compound of the above formula (XXIX) with the compound of the above formula (XXI) according to the process of Gupton et al., Tetrahedron, Vol. 43 (1987), p.1747, and if necessary, followed by converting $X^4$ into $X^1$, $X^2$, $X^3$ or amino group in a conventional manner.

Production 2

In the case of the compounds (I) wherein $R^2$ is optionally substituted benzoyl group and A is

the following reaction scheme may be employed.

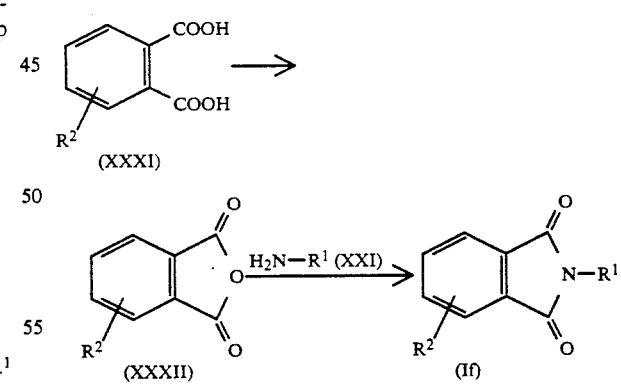

(in the above formulae, $R^1$ is as defined above).

Thus, the compound of the above formula (If), one of the objective compounds, can be prepared by dehydrating the compound of the above formula (XXXI) [obtained according to Paccal et al., J. Poly. Sci.; Part A; Poly. Chem., Vol. 26 (1988), p.865] with acetic anhydride or acetic anhydride/acetic acid under refluxing to give the compound of the above formula (XXXII) and reacting with the compound of the above formula (XXI) in the same manner as in the production d) above.

Production 3

In the case of the compounds (I) wherein $R^2$ is a group
of the formula (IV) and A is

the following reaction scheme may be employed.

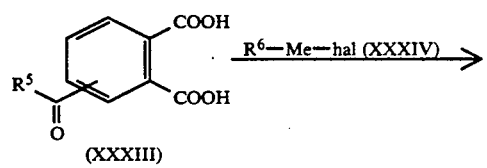

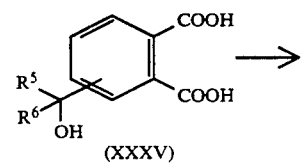

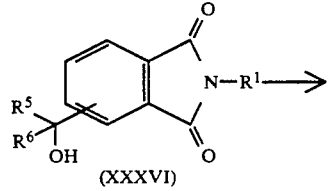

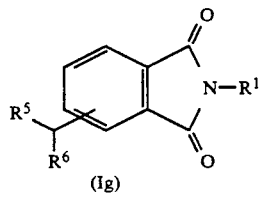

(in the above formulae, $R^1$, $R^5$ and $R^6$ are as defined above, and hal represents halogen atom).

Thus, the compound of the above formula (Ig), one of the objective compounds, can be prepared by reacting the compound of the above formula (XXXIII) with the compound of the above formula (XXXIV) in tetrahydrofuran or diethyl ether at temperature from room temperature to the boiling point of the solvent used to give the compound of the above formula (XXXV), converting it into the compound of the above formula (XXXVI) according to the process of Production 2, and reducing it with tin (II) chloride in conc. hydrochloric acid at temperature from room temperature to 70° C.

Production 4

In the case of the compounds (I) wherein A is —CH=CH—, the following reaction scheme may be employed.

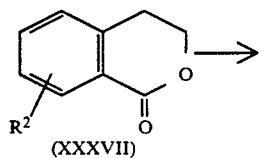

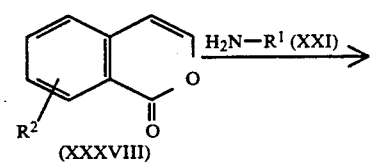

(in the above formulae, $R^1$ and $R^2$ are as defined above).

Thus, the compound of the above formula (Ih), one of the objective compounds, can be prepared by brominating the compound of the above formula (XXXVII) with N-bromosuccinimide and benzoyl peroxide in carbon tetrachloride under refluxing, subjecting to removal of hydrogen bromide with a base such as 1,8-diazabicyclo [5,4,0]undec-7-ene or the like, to give the compound of the formula (XXXVIII), and reacting the latter with the compound of the above formula (XXI).

The compound of the present invention may be administered solely or in combination with a pharmaceutically acceptable carrier, when used as a therapeutic agent. The weight ratio of the compound (I) with respect to the carrier may be determined depending upon solubility, chemical properties, route of administration, administering schedule or the like, of the compound.

For example, the compound may be orally administered in the form of granules, powders, tablets, hard capsules, soft capsules, syrups, emulsions, suspensions, solutions or the like, or intravenously, intramuscularly or subcutaneously in the form of injections.

Further, the compound may be used in the form of powders for injection and formulated just before use. Organic or inorganic, solid or liquid, carriers or diluents for pharmaceutical use suited for oral, rectal, parenteral or topical administration can be used together with the compound of the present invention. Examples of lubricants used in formulating the solid composition are lactose, sucrose, talc, cellulose, dextrin and the like, liquid formulations for oral administration such as emulsions, syrups, suspensions, solutions or the like, may include inert diluents, such as water, vegetable oils, and the like. Such formulations can include adjuvants other than inert diluents such as humectants, suspension aids, edulcorants, aroma, coloring agents, preservatives and the like. Liquid formulation may be encapsuled in a bio-degradable substance like gelatin Formulations for parenteral administration such as injections or the like may include solvents or suspending agents, for example propylene glycol, polyethylene glycol, benzyl alcohol, ethyl oleate, lecithin or the like. Such formulations can be prepared in a conventional manner.

In general, appropriate daily dosage of the compound of the present invention for adult is 0.01 to 1000 mg, preferably 0.01 to 100 mg, for oral use, and such dosage can be increased or decreased depending upon the age of a patient, conditions of the disease, symptoms, presence of other drugs to be administered at a time and the like. Said daily dosage of PAF antagonist may be administered once a day or in two or three divisions per day at appropriate intervals or intermittently.

When injected, an appropriate dosage of the compound of the present invention for adult ranges from 0.001 to 100 mg. Continuous or intermittent administration may be employed.

Specific examples of the compounds of the present invention will be illustratively shown below in Table 1 to Table 10.

TABLE 1

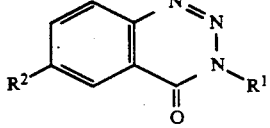

| Compound No. | R$^1$ | R$^2$ |
|---|---|---|
| 1 | 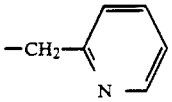 | 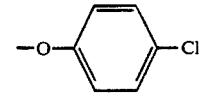 |
| 2 | 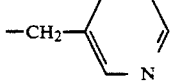 | 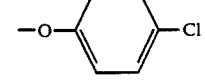 |
| 3 | 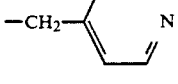 | 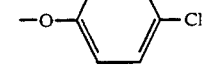 |
| 4 | 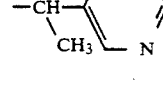 | 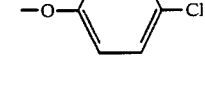 |
| 5 | 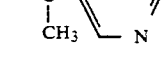 | 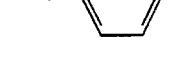 |
| 6 | 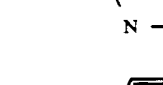 | 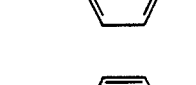 |
| 7 |  | 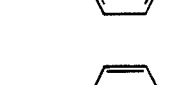 |
| 8 |  |  |
| 9 | 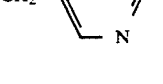 | 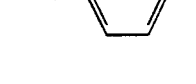 |

TABLE 1-continued

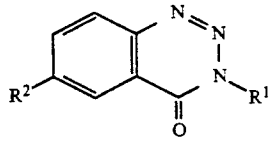

| Compound No. | R$^1$ | R$^2$ |
|---|---|---|
| 10 | 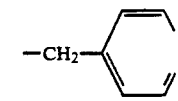 | 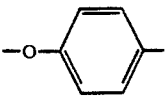 |
| 11 | 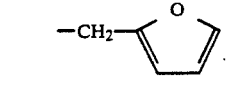 | 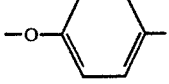 |
| 12 | 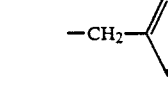 | 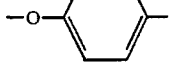 |
| 13 |  | 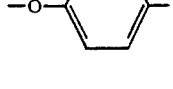 |
| 14 |  | 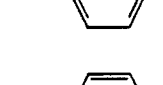 |
| 15 |  | 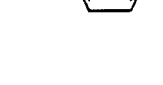 |
| 16 |  | 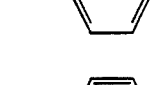 |
| 17 |  | 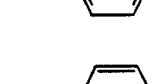 |
| 18 |  | 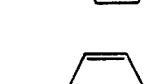 |
| 19 |  |  |
| 20 |  |  |

TABLE 1-continued

[Structure: R²-substituted benzene with N=N-N-R¹ triazene and C(=O) group]

| Compound No. | R¹ | R² |
|---|---|---|
| 21 | -CH₂-(3-pyridyl) | -O-C₆H₄-CN (4-) |

TABLE 2

[Structure: phthalimide with R² on benzene ring and R¹ on nitrogen]

| Compound No. | R¹ | R² |
|---|---|---|
| 22 | 3-pyridyl | -O-C₆H₄-Cl (4-) |
| 23 | 4-pyridyl | -O-C₆H₄-Cl (4-) |
| 24 | -CH₂-(2-pyridyl) | -O-C₆H₄-Cl (4-) |
| 25 | -CH₂-(3-pyridyl) | -O-C₆H₄-Cl (4-) |
| 26 | -CH₂-(4-pyridyl) | -O-C₆H₄-Cl (4-) |
| 27 | -CH(CH₃)-(3-pyridyl) | -O-C₆H₄-Cl (4-) |
| 28 | -C(CH₃)₂-(3-pyridyl) | -O-C₆H₄-Cl (4-) |
| 29 | -CH₂CH₂-(3-pyridyl) | -O-C₆H₄-Cl (4-) |
| 30 | -CH₂-(3-pyridyl) | -O-C₆H₄-Cl (3-) |

TABLE 2-continued

[Structure: phthalimide with N-R¹ and R² substituent on benzene ring]

| Compound No. | R¹ | R² |
|---|---|---|
| 31 | —CH₂-(3-pyridyl) | —O-(2-chlorophenyl) |
| 32 | —CH₂-(3-pyridyl) | —O-(4-fluorophenyl) |
| 33 | —CH₂-(3-pyridyl) | —O-(4-methylphenyl) |
| 34 | —CH₂-(3-pyridyl) | —O-(4-n-C₃H₇-phenyl) |
| 35 | —CH₂-(3-pyridyl) | —O-(4-OCH₃-phenyl) |
| 36 | —CH₂-(3-pyridyl) | —O-(3-OCH₃-phenyl) |
| 37 | —CH₂-(3-pyridyl) | —O-(2-OCH₃-phenyl) |
| 38 | —CH₂-(3-pyridyl) | —O-(4-OC₃H₇ⁿ-phenyl) |
| 39 | —CH₂-(3-pyridyl) | —O-(4-CF₃-phenyl) |
| 40 | —CH₂-(3-pyridyl) | —O-(4-CN-phenyl) |

TABLE 2-continued
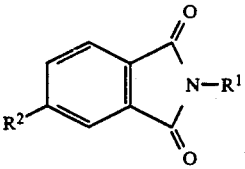
| Compound No. | R¹ | R² |
|---|---|---|
| 41 | 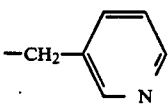 | 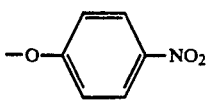 |
| 42 | 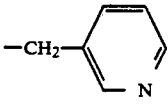 | 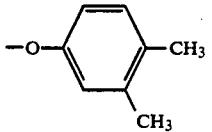 |
| 43 | 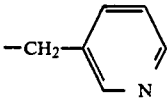 | 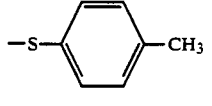 |
| 44 | 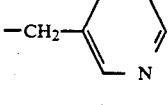 | 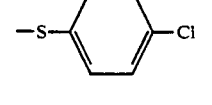 |
| 45 | 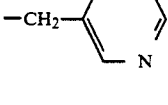 | 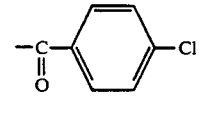 |
| 46 | 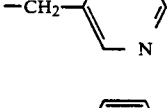 | 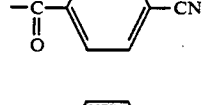 |
| 47 | 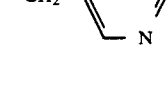 | 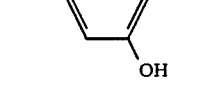 |
| 48 | 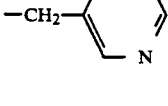 | 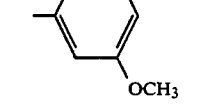 |
| 49 | 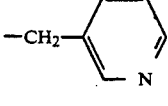 | 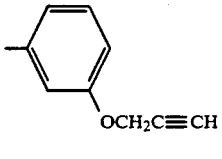 |
| 50 | 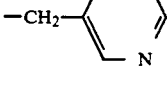 | 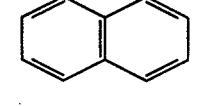 |

TABLE 2-continued

Structure: phthalimide with N–R¹ and R² on benzene ring

| Compound No. | R¹ | R² |
|---|---|---|
| 51 | –CH₂–(3-pyridyl) | C₆H₅–N(H)– |
| 52 | –CH₂–(3-pyridyl) | 4-Cl-C₆H₄–N(H)– |
| 53 | –CH₂–(3-pyridyl) | 4-F-C₆H₄–N(H)– |
| 54 | –CH₂–(3-pyridyl) | 4-CN-C₆H₄–N(H)– |
| 55 | –CH₂–(3-pyridyl) | 3,4-di-Cl-C₆H₃–N(H)– |
| 56 | –CH₂–(3-pyridyl) | C₆H₅–N(CH₃)– |
| 57 | –CH₂–(3-pyridyl) | 4-Cl-C₆H₄–N(C₃H₇$^i$)– |
| 58 | –CH₂–(3-pyridyl) | 4-Cl-C₆H₄–N(C₄H₉$^n$)– |
| 59 | –CH₂–(3-pyridyl) | (C₆H₅)₂N– |

TABLE 2-continued

[Structure: phthalimide core with R² substituent on benzene ring and N-R¹]

| Compound No. | R¹ | R² |
|---|---|---|
| 60 | -CH₂-(3-pyridyl) | -N(CH₃)(4-Cl-C₆H₄)₂ (bis(4-chlorophenyl)methylamino) |
| 61 | -CH₂-(3-pyridyl) | -N(CH₃)(4-F-C₆H₄)₂ |
| 62 | -CH₂-(3-pyridyl) | -N(CH₃)(4-Br-C₆H₄)₂ |
| 63 | -CH₂-(3-pyridyl) | -N(CH₃)(4-CN-C₆H₄)₂ |
| 64 | -CH₂-(3-pyridyl) | -N(CH₃)(4-NO₂-C₆H₄)₂ |
| 65 | -CH₂-(3-pyridyl) | -N(CH₃)(3,4-Cl₂-C₆H₃)₂ |
| 66 | -CH₂-(3-pyridyl) | -N(CH₃)(4-Cl-C₆H₄)(C₆H₅) |
| 67 | -CH₂-(3-pyridyl) | -N(CH₃)(4-Cl-C₆H₄)(C₆H₅) |
| 68 | -CH₂-(3-pyridyl) | -CH(4-Cl-C₆H₄)₂ |

TABLE 2-continued
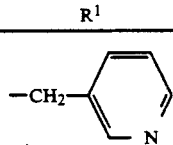
| Compound No. | R¹ | R² |
|---|---|---|
| 69 | -CH₂-(3-pyridyl) | 4-CH₃SO₂-C₆H₄-N(CH₃)-C₆H₄-4-SO₂CH₃ |
| 70 | -CH₂-(3-pyridyl N-oxide) | 4-NC-C₆H₄-N(CH₃)-C₆H₄-4-CN |
| 71 | -CH₂-(3-pyridyl N-oxide) | 4-Cl-C₆H₄-N(CH₃)-C₆H₄-4-Cl |
TABLE 3
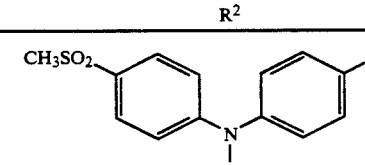
| Compound No. | R¹ | R² |
|---|---|---|
| 72 | -CH₂-(3-pyridyl) | -O-C₆H₄-4-Cl |
| 73 | -CH₂-(3-pyridyl) | -O-C₆H₄-3-Cl |
| 74 | -CH₂-(3-pyridyl) | -O-C₆H₄-2-Cl |
| 75 | -CH₂-(3-pyridyl) | -OCH₂-C₆H₄-4-Cl |
| 76 | -CH₂-(3-pyridyl) | -O-C₆H₄-4-CN |
| 77 | -CH₂-(3-pyridyl) | -NH-C₆H₄-4-Cl |
| 78 | -CH₂-(3-pyridyl) | -N(CH₃)-C₆H₄-4-Cl |

TABLE 3-continued

Structure: phthalimide with N–R¹ and R² substituent on benzene ring.

| Compound No. | R¹ | R² |
|---|---|---|
| 79 | —CH₂-(3-pyridyl) | —N(4-chlorophenyl)(4-chlorophenyl) |

TABLE 4

Structure: 3,4-dihydroisoquinolin-1(2H)-one with R² on benzene ring and N–R¹.

| Compound No. | R¹ | R² |
|---|---|---|
| 80 | —CH₂-(3-pyridyl) | —O-(4-NO₂-phenyl) |
| 81 | —CH₂-(3-pyridyl) | —O-(3-NO₂-phenyl) |
| 82 | —CH₂-(3-pyridyl) | —O-(2-NO₂-4-methyl-phenyl) |
| 83 | —CH₂-(3-pyridyl) | —O-phenyl |
| 84 | —CH₂-(3-pyridyl) | —O-(4-Cl-phenyl) |
| 85 | —CH₂-(3-pyridyl) | —O-(4-F-phenyl) |
| 86 | —CH₂-(3-pyridyl) | —O-(4-CH₃-phenyl) |
| 87 | —CH₂-(3-pyridyl) | —O-(4-CN-phenyl) |
| 88 | —CH₂-(3-pyridyl) | —O-(3-CN-phenyl) |
| 89 | —CH₂-(3-pyridyl) | —O-(2-CN-phenyl) |
| 90 | —CH₂-(3-pyridyl) | —O-(3,4-diF-phenyl) |
| 91 | —CH₂-(3-pyridyl) | —O-(3,4-diCH₃-phenyl) |
| 92 | —CH₂-(3-pyridyl) | —O-(4-OCH₃-phenyl) |
| 93 | —CH₂-(3-pyridyl) | —O-(4-COCH₃-phenyl) |
| 94 | —CH₂-(3-pyridyl) | —O-(4-CONH₂-phenyl) |
| 95 | —CH₂-(3-pyridyl) | —OCH₂-phenyl |
| 96 | —CH₂-(3-pyridyl) | —OCH₂-(4-Cl-phenyl) |

TABLE 4-continued

Structure: 7-R₂-substituted-2-R¹-3,4-dihydroisoquinolin-1(2H)-one

| Compound No. | R¹ | R² |
|---|---|---|
| 97 | -CH₂-(3-pyridyl) | -OCH₂-(3-Cl-C₆H₄) |
| 98 | -CH₂-(3-pyridyl) | -OCH₂-(2-Cl-C₆H₄) |
| 99 | -CH₂-(3-pyridyl) | -OCH₂-(4-F-C₆H₄) |
| 100 | -CH₂-(3-pyridyl) | -OCH₂-(2-F-C₆H₄) |
| 101 | -CH₂-(3-pyridyl) | -OCH₂-(2-Br-C₆H₄) |
| 102 | -CH₂-(3-pyridyl) | -OCH₂-(4-NO₂-C₆H₄) |
| 103 | -CH₂-(3-pyridyl) | -OCH₂-(3-NO₂-C₆H₄) |
| 104 | -CH₂-(3-pyridyl) | -OCH₂-(2-NO₂-C₆H₄) |
| 105 | -CH₂-(3-pyridyl) | -OCH₂-(2-CF₃-C₆H₄) |
| 106 | -CH₂-(3-pyridyl) | -OCH₂-(2-CH₃-C₆H₄) |
| 107 | -CH₂-(3-pyridyl) | -OCH₂-(2-C₂H₅-C₆H₄) |
| 108 | -CH₂-(3-pyridyl) | -OCH₂-(4-C₃H₇ⁱ-C₆H₄) |
| 109 | -CH₂-(3-pyridyl) | -OCH₂-(2-C₃H₇ⁱ-C₆H₄) |
| 110 | -CH₂-(3-pyridyl) | -OCH₂-(4-C₄H₉ⁿ-C₆H₄) |
| 111 | -CH₂-(3-pyridyl) | -OCH₂-(2,6-(CH₃)₂-C₆H₃) |
| 112 | -CH₂-(3-pyridyl) | -OCH₂-(2-CH₃O-C₆H₄) |
| 113 | -CH₂-(3-pyridyl) | -OCH₂-(2-CN-C₆H₄) |
| 114 | -CH₂-(3-pyridyl) | -OCH₂-(2-CH₂OH-C₆H₄) |
| 115 | -CH₂-(3-pyridyl) | -OCH₂-(2-CO₂CH₃-C₆H₄) |

TABLE 4-continued

Structure: R2-substituted benzene fused to -CH2-CH2-N(R1)-C(=O)- ring

| Compound No. | R¹ | R² |
|---|---|---|
| 116 | -CH2-(2-pyridyl) | -OCH2-phenyl(2-CO2CH3) |
| 117 | -CH2-(4-pyridyl) | -OCH2-phenyl(2-CO2CH3) |
| 118 | -CH2-(3-pyridyl) | -OCH2-phenyl(2-C(=O)N(CH3)2) |
| 119 | -CH2-(3-pyridyl) | -OCH2-phenyl(2-SO2CH3) |
| 120 | -CH(CH3)-(3-pyridyl) | -OCH2-phenyl |
| 121 | 3-pyridyl | -O-phenyl(4-Cl) |
| 122 | -CH2-(pyrimidinyl) | -OCH2-phenyl(2-NO2) |

TABLE 5

Structure: R2-substituted benzene fused to -CH2-CH2-N(R1)-C(=O)- (isoquinolinone)

| Compound No. | R¹ | R² |
|---|---|---|
| 123 | -CH2-(3-pyridyl) | -OCH2-phenyl(2-NO2) |
| 124 | -CH2-(3-pyridyl) | -O-phenyl(3-NO2) |

TABLE 6

Structure: R2-substituted benzene fused to -CH2-N(R1)-C(=O)- (isoindolinone)

| Compound No. | R¹ | R² |
|---|---|---|
| 125 | -CH2-(3-pyridyl) | -O-phenyl(4-F) |

TABLE 7

Structure: R2-substituted isoindolinone

| Compound No. | R¹ | R² |
|---|---|---|
| 126 | -CH2-(3-pyridyl) | -O-phenyl(4-Cl) |
| 127 | -CH2-(4-pyridyl) | -O-phenyl(4-Cl) |

TABLE 8

Structure: R2-substituted benzene fused to -CH=CH-N(R1)-C(=O)- (isoquinolinone unsaturated)

| Compound No. | R¹ | R² |
|---|---|---|
| 128 | -CH2-(3-pyridyl) | -O-phenyl(4-Cl) |

TABLE 8-continued

[Structure: R²-substituted isoquinolin-1(2H)-one with N-R¹]

| Compound No. | R¹ | R² |
|---|---|---|
| 129 | -CH₂-(3-pyridyl) | -O-(4-methylphenyl) |
| 130 | -(3-pyridyl) | -O-(4-chlorophenyl) |

TABLE 9

[Structure: R²-substituted 1,2,3-benzotriazin-4(3H)-one with N-R¹]

| Compound No. | R¹ | R² |
|---|---|---|
| 131 | -CH₂-(3-pyridyl) | -O-(4-chlorophenyl) |

TABLE 10

[Structure: R²-substituted phthalazin-1(2H)-one with N-R¹]

| Compound No. | R¹ | R² |
|---|---|---|
| 132 | -CH₂-(3-pyridyl) | -O-(4-chlorophenyl) |

The present invention is explained in detail below by examples and experiments, but the present invention is not limited to those examples and experiments. The abbreviation "NMR" in examples means Nuclear Magnetic Resonance, and the solvent within the parensis of [NMR] means a solvent used for measurement. The unit is ppm.

Further, Compound No. described in Table 11–14 corresponds to Compound No. described in Table 1–10.

EXAMPLE 1

(1) Preparation of 6-(4-chlorophenoxy)-3-(3-pyridylmethyl)-1,2,3-benzotriazin-4 (3H)-one (Compound No. 2 in Table)

a) Preparation of 2-amino-5-bromo-N-(3-pyridylmethyl)benzamide:

In 238 ml of dimethylformamide were dissolved 23.8 g of 2-amino-5-bromobenzoic acid, 13.1 g of 3-aminomethylpyridine and 24.5 g of triethylamine, and the solution was chilled with ice. To this solution was dropwise added 33.3 g of diphenylphosphoryl azide in 10 minutes, and the resultant mixture was stirred at room temperature for 18 hours. The reaction mixture was poured onto ice water. The precipitated solid was filtered, washed with water and dried to give 29.4 g of the titled compound.

$^1$HNMR (CDCl₃) δ: 4.59 (d, 2H J=6Hz). 5.57 (s, 2H), 6.58 (d, 1H, J=9Hz), 6.70 (broad s, 1H), 7.25–7.31 (m, 2H), 7.45 (d, 1H, J=2Hz), 7.67–7.72 (m, 1H), 8.51–8.57 (m, 2H).

b) Preparation of 6-bromo-3-(3-pyridylmethyl)-1,2,3-benzotriazin-4 (3H)-one:

To a mixture of 29.4 g of 2-amino-5-bromo-N-(3-pyridylmethyl) benzamide, 32 ml of conc. hydrochloric acid and 400 ml of water was dropwise added a solution of 6.83 g and 400 ml of water was dropwise added a solution of 6.83 g of sodium nitrite and 48 ml of water at 0° to 2° C. The resultant mixture was stirred at 0° to 2° C. for 45 minutes, neutralized with 1 N aqueous sodium hydroxide and shaken with chloroform. The organic layer was washed with saturated brine, dried over anhydrous magnesium sulfate, and concentrated in vacuo to give 25.6 g of the titled compound.

$^1$HNMR (CDCl₃) δ: 5.63 (s, 2H), 7.25–7.31 (m, 1H), 7.84–8.05 (m, 2H), 8.03 (s, 1H), 8.47–8.81 (m, 3H ).

c) Preparation of 6-(4-chlorophenoxy)-3-(3-pyridylmethyl)-1,2,3-benzotriazin-4 (3H)-one:

A mixture of 10.0 g of 6-bromo-3-(3-pyridylmethyl)-1,2,3-benzotriazin-4 (3H)-one, 6.1 g of 4-chlorophenol, 9.4 g of cupric oxide, 13.1 g of potassium carbonate and 100 ml of pyridine was refluxed under heating for 9 hours. After finishing the reaction, the insoluble material was filtered off, and the filtrate was concentrated in vacuo. The resulting residue was chromatographed on a column of silica gel, developing with ethyl acetate/hexane=1:1 and then recrystallized from hexane - methylene chloride to give 5.68 g of the titled compound.

mp. 134°–136° C.

The following compounds were prepared in the same manner as in Example 1 (1).

(2) 6-(4-chlorophenoxy)-3-(2-pyridylmethyl)-1,2,3-benzotriazin-4 (3H)-one (Compound No. 1 in Table) mp. 108.5°–110.5° C.

(3) 6-(4-chlorophenoxy)-3-(4-pyridylmethyl)-1,2,3-benzotriazin-4 (3H)-one hydrochloride (Compound No. 3 in Table)
mp. 149°–156° C.

(4) 6-(4-chlorophenoxy)-3-[1-(3-pyridyl) ethyl]-1,2,3-benzotriazin-4 (3H)-one hydrochloride (Compound No. 4 in Table)
mp. 160°–163° C.

(5) 6-(4-chlorophenoxy)-3-[2-(2-pyridyl) ethyl]-1,2,3-benzotriazin-4 (3H)-one (Compound No. 6 in Table)
mp. 99°–101.5° C.

(6) 6-(4-chlorophenoxy)-3-[5-(2-methylpyridyl) methyl]-1,2,3-benzotriazin-4 (3H)-one (Compound No. 8 in Table)
$^1$HNMR (CDCl₂) δ: 2.52 (s. 3H), 5.55 (s, 2H), 7.02–7.13 (m, 3H), 7.38–7.42 (m, 2H), 7.57–7.61 (m, 2H), 7.71–7.75 (m, 1H), 8.13–8.16 (m, 1H), 8.66 (broads 1H).

(7) 6-(4-chlorophenoxy)-3-[5-(2-methoxypyridyl) methyl]-1,2,3-benzotriazin-4 (3H)-one (Compound No. 9 in Table)
mp. 121.5°–124° C.

(8) 4-[[6-(4-chlorophenoxy)-4-oxo-3H-1,2,3-benzotriazin-3-yl]methyl]pyridin-1-oxide (Compound No. 10 in Table)
mp. 177°–179° C.

(9) 6-(4-chlorophenoxy)-3-(2-furylmethyl)-1,2,3-benzotriazin-4 (3H)-one (Compound No. 11 in Table)
mp. 170.5°–171.5° C.

(10) 6-(4-chlorophenoxy)-3-(3-furylmethyl)-1,2,3-benzotriazin-4 (3H)-one (Compound No. 12 in Table)
mp. 94°–98° C.

(11) 6-(4-chlorophenoxy)-3-(2-thienylmethyl)-1,2,3-benzotriazin-4 (3H)-one (Compound No. 13 in Table)
mp. 164.5°–165° C.

(12) 6-(4-chlorophenoxy)-3-(4-imidazolylmethyl)-1,2,3-benzotriazin-4 (3H)-one (Compound No. 14 in Table)
mp. 191°–196° C.

(13) 6-(4-chlorophenoxy)-3-[4(5-mehylimidazolyl) methyl])-1,2,3-benzotriazin-4 (3H)-one (Compound No. 15 in Table)
mp. 184°–186° C.

(14) 6-(4-chlorophenoxy)-3-(4-pyrazolylmethyl)-1,2,3-benzotriazin-4 (3H)-one (Compound No. 16 in Table)
mp. 199°–201.5° C.

(15) 6-(4-chlorophenoxy)-3-[2-(4-imidazolyl) ethyl]-1,2,3-benzotriazin-4 (3H)-one (Compound No. 17 in Table)
mp. 197°–199.5° C.

(16) 6-(4-fluorophenoxy)-3-(3-pyridylmethyl)-1,2,3-benzotriazin-4 (3H)-one (Compound No. 18 in Table)
mp. 134°–135.5° C.

(17) 6-(4-methylphenoxy)-3-(3-pyridylmethyl)-1,2,3-benzotriazin-4 (3H)-one (Compound No. 19 in Table)
mp. 134.5°–136° C.

(18) 6-(4-butylphenoxy)-3-(3-pyridylmethyl)-1,2,3-benzotriazin-4 (3H)-one hydrochloride (Compound No. 20 in Table)
mp. 102°–107° C.

(19) 6-(4-cyanophenoxy)-3-(3-pyridylmethyl)-1,2,3-benzotriazin-4 (3H)-one (Compound No. 21 in Table)
$^1$H NMR (CDCl$_3$) δ: 5.62 (s, 2H), 7.10–7.28 and 7.50–7.90 (m, total 8H), 8.22 (d, 1H, J=8 Hz), 8.57–8.59 (m, 1H), 8.78–8.79 (m, 1H).

EXAMPLE 2

Preparation of 4-(4-chlorophenoxy)-2-(3-pyridylmethyl)-1H-isoindole-1,3 (2H)-dione (Compound No. 72 in Table)

a) Preparation of 4-nitro-2-(3-pyridylmethyl)-1H-isoindole-1,3 (2H)-dione:

To a mixture of 15.0 g of 3-nitrophthalic acid anhydride, 233 ml of acetic acid and 80 ml of toluene was added 10.1 g of 3-aminomethylpyridine, and the resultant mixture was refluxed for 1.5 hours under heating. The reaction mixture was concentrated in vacuo, diluted with ethyl acetate, washed with 1N aqueous sodium hydroxide and water in order, dried over anhydrous magnesium sulfate and concentrated in vacuo to give 20.6 g of the titled compound.

$^1$H NMR (CDCl$_3$) δ: 4.89 (s, 2H), 7.25–7.38 (m, 1H), 7.77–7.82 (m, 1H), 7.90–7.96 (m, 1H), 8.12–8.15 (m, 2H), 8.54–8.56 (m, 1H), 8.71–8.72 (m, 1H).

b) Preparation of 4-(4-chlorophenoxy)-2-(3-pyridylmethyl)-1H-isoindole-1,3 (2H)-dione:

A mixture of 591 mg of 4-chlorophenol, 184 mg of sodium hydroxide, 0.6 ml of water, 30 ml of dimethyl sulfoxide and 10 ml of toluene was refluxed under heating, using Deen Stark's azeotropic distillator to evaporate water and toluene completely. To the residual mixture was added 1.24 g of 4-nitro-2-(3-pyridylmethyl)-1H-isoindole-1,3 (2H)-dione, and the mixture was stirred at 100° C. for 3 hours. After cooling, the reaction mixture was poured into water and shaken with methylene chloride. The organic layer was washed with water, dried over anhydrous magnesium sulfate and concentrated in vacuo. The resulting residue was chromatographed on a column of silica gel, eluting with ethyl acetate to give 1.17 g of the titled compound.
mp. 193°–194.5° C.

The following compounds were prepared in the same manner as in Example 2 (1).

(2) 5-(4-chlorophenoxy)-2-(3-pyridyl)-1H-isoindole-1,3 (2H)-dione (Compound No. 22 in Table)
mp. 201°–202° C.

(3) 5-(4-chlorophenoxy)-2-(4-pyridyl)-1H-isoindole-1,3 (2H)-dione (Compound No. 23 in Table)
mp. 172.5°–173.5° C.

(4) 5-(4-chlorophenoxy)-2-(2-pyridylmethyl)-1H-isoindole-1,3 (2H)-dione (Compound No. 24 in Table)
mp. 117°–119° C.

(5) 5-(4-chlorophenoxy)-2-(3-pyridylmethyl)-1H-isoindole-1,3 (2H)-dione (Compound No. 25 in Table)
mp. 119°–121° C.

(6) 5-(4-chlorophenoxy)-2-(4-pyridylmethyl)-1H-isoindole-1,3 (2H)-dione (Compound No. 26 in Table)
mp. 89°–90° C.

(7) 5-(2-chlorophenoxy)-2-(3-pyridylmethyl)-1H-isoindole-1,3 (2H)-dione (Compound No. 31 in Table)
$^1$H NMR (CDCl$_3$) δ: 4.83 (s, 2H), 7.13–7.34 (m, 6H), 7.50 (dd, 1H), 7.33–7.82 (m, 2H), 8.51 (dd, 1H), 8.68 (d, 1H)

(8) 5-(4-fluorophenoxy)-2-(3-pyridylmethyl)-1H-isoindole-1,3 (2H)-dione (Compound No. 32 in Table)
mp 111°–113° C.

(9) 5-(4-methylphenoxy)-2-(3-pyridylmethyl)-1H-isoindole-1,3 (2H)-dione (Compound No. 33 in Table)
mp. 133°–137° C.

(10) 5-(4-propylphenoxy)-2-(3-pyridylmethyl)-1H-isoindole-1,3 (2H)-dione (Compound No. 34 in Table)
$^1$H NMR (CDCl$_3$) δ: 0.94 (t, 3H), 1.69 (m, 2H), 2.61 (t, 2H), 4.82 (s, 2H), 6.97 (dd, 2H), 7.20–7.31 (m, 5H), 7.72–7.79 (m, 2H), 8.52 (dd, 1H), 8.69 (d, 1H)

(11) 5-(2-methoxyphenoxy)-2-(3-pyridylmethyl)-1H-isoindole-1,3 (2H)-dione (Compound No. 37 in Table)
$^1$H NMR (CDCl$_3$) δ: 3.77 (s, 3H), 4.81 (s, 2H), 7.00–7.08 (m, 3H), 7.20–7.26 (m, 4H), 7.73–7.78 (m, 2H), 8.52 (dd, 1H), 8.68 (d, 1H)

(12) 5-(4-propoxyphenoxy)-2-(3-pyridylmethyl)-1H-isoindole-1,3 (2H)-dione (Compound No. 38 in Table)
mp. 89°–91° C.

(13) 5-(4-trifluoromethylphenoxy)-2-(3-pyridylmethyl)-1H-isoindole-1,3 (2H)-dione (Compound No. 39 in Table)
mp. 122°–125° C.

(14) 5-(4-cyanophenoxy)-2-(3-pyridylmethyl)-1H-isoindole-1,3 (2H)-dione (Compound No. 40 in Table)
mp. 138°–140° C.

(15) 5-(3,4-dimethylphenoxy)-2-(3-pyridylmethyl)-1H-isoindole-1,3 (2H)-dione (Compound No. 42 in Table)
mp. 121°–123° C.

(16) 4-(3-chlorophenoxy)-2-(3-pyridylmethyl)-1H-isoindole-1,3 (2H)-dione (Compound No. 73 in Table)
mp. 117.5°–118.5° C.

(17) 4-(2-chlorophenoxy)-2-(3-pyridylmethyl)-1H-isoindole-1,3 (2H)-dione (Compound No. 74 in Table)

¹H NMR (CDCl₃) δ: 4.86 (s, 2H), 6.83–6.86 (m, 1H), 7.15–7.33 (m, 4H), 7.48–7.61 (m, 3H), 7.79–7.83 (m, 1H), 8.52–8.55 (m, 1H), 8.73–8.74 (m, 1H)

(18) 4-(4-cyanophenoxy)-2-(3-pyridylmethyl)-1H-isoindole-1,3 (2H)-dione (Compound No. 76 in Table) mp. 177°–179° C.

EXAMPLE 3

(1) Preparation of 5-[N,N-bis (4-cyanophenyl) amino]-2-(3-pyridylmethyl)-1H-isoindole-1,3 (2H)-dione (Compound No. 63 in Table)

a) Preparation of 5-nitro-2-(3-pyridylmethyl)-1H-isoindole-1,3 (2H)-dione:

The titled compound was obtained from 4-nitrophthalic acid anhydride and 3-aminomethylpyridine in the same manner as in Example 2 (1) a).

mp. 128°–131° C.

(b) Preparation of 5-amino-2-(3-pyridylmethyl)-1H-isoindole-1,3 (2H)-dione:

To 200 ml of conc. hydrochloric acid was added 21.1 g of stannous chloride under ice cooling, and 9.0 g of 5-nitro-2-(3-pyridylmethyl)-1H-isoindole-1,3 (2H)-dione was added. The reaction mixture was stirred at room temperature for 15 minutes and stirred at 80° C. for 30 minutes. After cooling, the mixture was filtered, and the resultant solid was mixed with water and made alkaline with aqueous ammonia. To this mixture was added 500 ml of tetrahydrofuran, and the resultant mixture was filtered with celite. The filtrate was shaken with methylene chloride. The organic layer was washed with water, dried over anhydrous magnesium sulfate and concentrated in vacuo. The resultant residue was chromatographed on a column of silica gel, eluting with ethyl acetate and hexane (2:1) to give 7.4 g of the titled compound.

¹H NMR (DMSO$_{d6}$) δ: 4.72 and 4.75 (a pair of s, 2H), 6.52 and 9.43 (a pair of s, 2H), 6.79–7.71 (m, 5H), 8.47–8.56 (m, 2H)

c) Preparation of 5-[N,N-bis (4-cyanophenyl) amino]-2-(3-pyridylmethyl)-1H-isoindole-1,3 (2H)-dione:

A mixture of 134 mg of 5-amino-2-(3-pyridylmethyl)-1H-isoindole-1,3 (2H)-dione, 302 g of 4-iodobenzonitrile, 135 mg of copper dust, 28 mg of 18-crown-6 (1,4,7,10,13,16-hexaoxacyclooctadecane), 585 mg of potassium carbonate and 3 ml of 1,2-dichlorobenzene was refluxed under heating for 8 hours. After finishing the reaction, the insoluble material was filtered off, and the filtrate was concentrated in vacuo. The resulting residue was chromatographed on a column of silica gel, eluting with chloroform and methanol (40:1) to give 149 mg of the titled compound.

mp. 208°–212° C.

The following compounds were prepared in the same manner as in Example 3 (1).

(2) 5-(N,N-diphenylamino)-2-(3-pyridylmethyl)-1H-isoindole-1,3 (2H)-dione (Compound No. 59 in Table)

¹H NMR (CDCl₃) δ: 4.80 (s, 2H), 7.13–7.38 (m, 13H), 7.59 (d, 1H), 7.72–7.75 (m, 1H), 8.51 (dd, 1H), 8.68 (d, 1H)

(3) 5-[N,N-bis (4-chlorophenyl) amino]-2-(3-pyridylmethyl)-1H-isoindole-1,3 (2H)-dione (Compound No. 60 in Table)
mp. 161°–163° C.

(4) 5-[N,N-bis (4-fluorophenyl) amino]-2-(3-pyridylmethyl)-1H-isoindole-1,3 (2H)-dione (Compound No. 61 in Table)

¹H NMR (CDCl₃) δ: 4.81 (s, 2H), 7.03–7.17 (m, 9H), 7.23–7.28 (m, 2H ), 7.43 (d, 1H), 7.57 (m, 1H), 8.50 (dd, 1H), 8.65 (d, 1H)

(5) 5-[N,N-bis (3,4-dichlorophenyl) amino]-2-(3-pyridylmethyl)-1H-isoindole-1,3 (2H)-dione (Compound No. 65 in Table)
mp. 97°–100° C.

(6) 4-[N,N-bis (4-chlorophenyl) amino]-2-(3-pyridylmethyl)-1H-isoindole-1,3 (2H)-dione (Compound No. 79 in Table)
mp. 167°–168.5° C.

(7) 5-[N,N-bis (4-methanesulfonylphenyl) amino]-2-(3-pyridylmethyl)-1H-isoindole-1,3 (2H)-dione (Compound No. 69 in Table)
mp. 149°–152° C.

EXAMPLE 4

(1) Preparation of 5-[N-(4-chlorophenyl) amino]-2-(3-pyridylmethyl)-1H-isoindole-1,3-dione (Compound No. 52 in Table)

A mixture of 260 mg of 5-amino-2-(3-pyridylmethyl)-1H-isoindole-1,3-(2H)-dione, 296 mg of 1-chloro-4-iodobenzene, 131 mg of copper dust, 54 mg of 18-crown-6 (1,4,7,10,13,16-hexaoxacyclooctadecane), 569 mg of potassium carbonate and 4 ml of 1,2-dichlorobenzene was refluxed under heating for 1 hour. After finishing the reaction, the insoluble material was filtered off, and the filtrate was concentrated in vacuo. The resultant residue was chromatographed on a column of silica gel, eluting with chloroform and methanol (20:1) to give 185 mg of the titled compound.

mp. 207°–209.5° C.

The following compounds were prepared in the same manner as in Example 4 (1).

(2) 5-[N-phenylamino]-2-(3-pyridylmethyl)-1H-isoindole-1,3 (2H)-dione (Compound No. 51 in Table)
mp. 172°–173° C.

(3) 5-[N-(4-fluorophenyl) amino]-2-(3-pyridylmethyl)-1H-isoindole-1,3 (2H)-dione (Compound No. 53 in Table)
mp. 190°–196° C.

(4) 5-[N-(4-cyanophenyl) amino]-2-(3-pyridylmethyl)-1H-isoindole-1,3 (2H)-dione (Compound No. 54 in Table)
mp. 222°–225° C.

(5) 5-[N-(3,4-dichlorophenyl) amino]-2-(3-pyridylmethyl)-1H-isoindole-1,3 (2H)-dione (Compound No. 55 in Table)
mp. 227°–229° C.

(6) 4-[N-(4-chlorophenyl) amino]-2-(3-pyridylmethyl)-1H-isoindole-1,3 (2H)-dione (Compound No. 77 in Table)
mp. 156°–158° C.

EXAMPLE 5

(1) Preparation of 5-[N-(4-chlorophenyl)-N-phenylamino]-2-(3-pyridylmethyl)-1H-isoindole-1,3 (2H)-dione (Compound No. 66 in Table)

A mixture of 85 mg of 5-[N-(4-chlorophenyl) amino]-2-(3-pyridylmethyl)-1H-isoindole-1,3 (2H)-dione, 71 mg of iodobenzene, 30 mg of copper dust, 12 mg of 18-crown-6 (1,4,7,10,13,16-hexaoxacyclooctadecane), 128 mg of potassium carbonate and 2 ml of 1,2-dichlorobenzene was refluxed under heating for 7 hours. After finishing the reaction, the insoluble material was filtered off, and the filtrate was concentrated in vacuo. The resultant residue was chromatographed on a column of silica gel, eluting with chloroform and methanol (100:1) to give 96 mg of the titled compound.

$^1$H NMR (CDCl$_3$) δ: 4.81 (s, 2H), 7.06–7.39 (m, 12H), 7.61 (d, 1H, J=8 Hz), 7.73–7.76 (m, 1H), 8.52–8.68 (m, 2H)

The following compounds were prepared in the same manner as in Example 5 (1).

(2) 5-(N-methyl-N-phenylamino)-2-(3-pyridylmethyl)-1H-isoindole-1,3 (2H)-dione (Compound No. 56 in Table)
mp. 135°–138° C.

(3) 5-[N-isopropyl-N-(4-chlorophenyl) amino]-2-(3-pyridylmethyl)-1H-isoindole-1,3 (2H)-dione (Compound No. 57 in Table)
mp. 110°–114° c.

(4) 5-[N-butyl-N-(4-fluorophenyl) amino]-2-(3-pyridylmethyl)-1H-isoindole-1,3 (2H)-dione (Compound No. 58 in Table)
mp. 90°–93° C.

(5) 4-[N-methyl-N-(4-chlorophenyl) amino]-2-(3-pyridylmethyl)-1H-isoindole-1,3 (2H)-dione (Compound No. 78 in Table)
mp. 80°–83° C.

EXAMPLE 6

(1) Preparation of 5-(4-chlorophenylthio)-2-(3-pyridylmethyl)-1H-isoindole-1,3 (2H)-dione (Compound No. 44 in Table)

To a suspension of 42 mg of sodium hydride (about 60%) in 10 ml of dimethylformamide was added 150 mg of 4-chlorothiophenol, and the resultant mixture was stirred at 60° C. for 30 minutes and mixed with 300 mg of 5-nitro-2-(3-pyridylmethyl)-1H-isoindole-1,3 (2H)-dione. The mixture was heated at 120° C. for 8 hours under stirring, mixed with water and shaken with ethyl acetate. The organic layer was dried over anhydrous sodium sulfate, concentrated in vacuo, and the resultant residue was chromatographed on a column of silica gel, eluting with chloroform to give 201 mg of the titled compound.
mp. 115°–118° C.

The following compounds were prepared in the same manner as in Example 6 (1).

(2) 5-(4-methylphenylthio)-2-(3-pyridylmethyl)-1H-isoindole-1,3 (2H)-dione (Compound No. 43 in Table)
mp. 88°–90° C.

EXAMPLE 7

Preparation of 5-(4-chlorobenzoyl)-2-(3-pyridylmethyl)-1H-isoindole-1,3 (2H)-dione (Compound No. 45 in Table)

a) Preparation of 4-(4-chlorobenzoyl) phthalic acid anhydride:

To 10 ml of acetic acid were added 1.00 g of 4-(4-chlorobenzoyl) phthalic acid and 1.34 g of acetic anhydride, and the resultant mixture was refluxed under heating for 3.5 hours. After finishing the reaction, the acetic acid was evaporated in vacuo and the resultant residue was mixed with hexane. The precipitated solid was filtered, washed with hexane and dried to give 0.91 g of the titled compound.

$^1$H NMR (CDCl$_3$) δ: 7.54 (d, 2H, J=7 Hz), 7.76 (d, 2H, J=7 Hz), 8.17 (d, 1H, J=8 Hz), 8.29 (d, 1H, J=8 Hz), 8.32 (s, 1H).

b) Preparation of 5-(4-chlorobenzoyl)-2-(3-pyridylmethyl)-1H-isoindole-1,3 (2H)-dione:

To a mixture of 870 mg of 4-(4-chlorobenzoyl) phthalic acid anhydride, 10 ml of acetic acid and 10 ml of toluene was added 394 mg of 3-aminomethylpyridine, and the resultant mixture was refluxed under heating for 2 hours. The reaction mixture was concentrated in vacuo, and the resultant residue was chromatographed on a column of silica gel, eluting with ethyl acetate to give 1.11 g of the titled compound.
mp. 132°–134° C.

EXAMPLE 8

Preparation of 5-[bis (4-chlorophenyl) methyl]-2-(3-pyridylmethyl)-1H-isoindole-1,3 (2H)-dione (Compound No. 68 in Table)

a) Preparation of 5-[hydroxybis (4-chlorophenyl) methyl]-2-(3-pyridylmethyl)-1H-isoindole-1,3-dione:

To a solution of 2.00 g of 4-(4-chlorobenzoyl) phthalic acid in 63 ml of tetrahydrofuran was dropwise added 50 ml of ether solution (0.59M) of 4-chlorophenylmagnesium bromide at room temperature in 20 minutes. The reaction mixture was refluxed under heating for 3 hours, cooled with ice, hydrolyzed with 10% hydrochloric acid and shaken with ethyl acetate. The organic layer was washed with water, dried over anhydrous magnesium sulfate and concentrated in vacuo. The resultant residue was chromatographed on a column of silica gel, eluting with chloroform and methanol (2:1) to give crude 4-[hydroxybis (4-chlorophenyl) methyl]phthalic acid. This intermediate was provided for the following reaction without further purification.

A mixture of 3.1 ml of acetic anhydride, 20 ml of acetic acid and crude alcohol obtained in the above step was refluxed under heating for 2 hours, and after termination of the reaction, the mixture was concentrated in vacuo, and the resultant residue was mixed with 10 ml of acetic acid and 1.42 g of 3-aminomethylpyridine and refluxed under heating for 1 hour. The reaction mixture was concentrated in vacuo, and diluted with ethyl acetate. The organic layer was washed with water, saturated aqueous sodium bicarbonate and saturated brine, dried over anhydrous magnesium sulfate and concentrated in vacuo. The resultant residue was chromatographed on a column of silica gel, eluting with ethyl acetate and hexane (1:1) to give 1.64 g of the titled compound.

$^1$H NMR (CDCl$_3$) δ: 4.79 (s, 2H), 7.17–7.82 (m, 13H), 8.34–8.37 (m, 1H), 8.52–8.53 (m, 1H)

b) Preparation of 5-[bis (4-chlorophenyl) methyl]-2-(3-pyridylmethyl)-1H-isoindole-1,3 (2H)-dione:

To 12 ml of conc. hydrochloric acid were added 546 mg of stannous chloride and 352 mg of 5-[hydroxybis (4-chlorophenyl) methyl]-2-(3-pyridylmethyl)-1H-isoindole-1,3-dione, and the resultant mixture was stirred at 70° C. for 1.5 hours. After ice cooling, the reaction mixture was made alkaline with 1N aqueous sodium hydroxide and shaken with methylene chloride. The organic layer was washed with water, dried over anhydrous magnesium sulfate, and the resultant residue was chromatographed on a column of silica gel, eluting with ethyl acetate and hexane (1:1) to give 188 mg of the titled compound.

$^1$H NMR (CDCl$_3$) δ: 4.83 (s, 2H), 5.61 (s, 1H), 6.99 (d, 4H, J=7 Hz), 7.21–7.31 (m, 1H ), 7.30 (d, 4H, J=7 Hz), 7.44–7.48 (m, 1H), 7.56 (s, 1H), 7.73–7.79 (m, 2H), 8.50–8.53 (m, 1H), 8.68–8.89 (m, 1H)

EXAMPLE 9

(1) Preparation of 5-(3-methoxyphenyl)-2-(3-pyridylmethyl)-1H-isoindole-1,3 (2H)-dione (Compound No. 48 in Table)

To a solution of 1.80 g of zinc chloride in 8.8 ml of tetrahydrofuran was added 8.8 ml of tetrahydrofuran solution (1.0M) of 3-methoxyphenylmagnesium bromide, and the resultant mixture was stirred at room temperature for 20 minutes. This solution was added to a mixture of 2.27 g of 2-(3-pyridylmethyl)-5-(trifluoromethanesulfonyloxy)-1H-isoindole-1,3 (2H)-dione, 27 mg of palladium acetate, 131 mg of 1,1'-bis(diphenylphosphino) ferrocene and 18 ml of tetrahydrofuran and stirred at room temperature for 17 hours. After finishing the reaction, the mixture was mixed with water under ice cooling and shaken with ethyl acetate. The organic layer was washed with water and saturated brine in order, dried over anhydrous magnesium sulfate and concentrated in vacuo. The resultant residue was chromatographed on a column of silica gel, eluting with ethyl acetate and hexane (1:3) to (1:1) to give 1.71 g of the titled compound.

mp. 115°–117° C.

The following compounds were prepared in the same manner as in Example 9 (1).

(2) 5-(1-naphthyl)-2-(3-pyridylmethyl)-1H-isoindole-1,3 (2H)-dione (Compound No. 50 in Table)
$^1$H NMR (CDCl$_3$) δ: 4.88 (s, 2H), 7.13–7.97 (m, 12H), 8.52–8.55 (m, 1H), 8.74–8.75 (m, 1H).

EXAMPLE 10

(1) Preparation of 7-(4-chlorophenoxy)-3,4-dihydro-2-(3-pyridylmethyl)-1 (2H)-isoquinolinone (Compound No. 84 in Table):

a) Preparation of 3,4-dihydro-7-methoxy-2-(3-pyridylmethyl)-1 (2H)-isoquinolinone:

To a suspension of 3.70 g of sodium hydride (about 60%) in 80 ml of dimethylformamide was added portionwise 5.30 g of 3-chloromethylpyridine hydrochloride under ice cooling. The mixture was stirred under ice cooling for 15 minutes, and a solution of 4.09 g of 3,4-dihydro-7-methoxy-1 (2H)-isoquinolinone in 30 ml of dimethylformamide was added dropwise in 15 minutes thereto. The mixture was stirred at 10° C. for 1 hour, mixed with water and shaken with toluene. The organic layer was washed with water, dried over anhydrous magnesium sulfate and concentrated in vacuo. The resultant residue was chromatographed on a column of silica gel, eluting with ethyl acetate to give 4.50 g of the titled compound.

$^1$H NMR (CDCl$_3$) δ: 2.90 (t, 2H, J=7 Hz), 3.50 (t, 2H, J=7 Hz), 3.86 (s, 3H), 4.80 (s, 2H), 6.93–7.01 (m, 1H), 7.07–7.10 (m, 1H), 7.25–7.31 (m, 1H), 7.66–7.78 (m, 2H), 8.53–8.60 (m, 2H).

b) Preparation of 3,4-dihydro-7-hydroxy-2-(3-pyridylmethyl)-1 (2H)-isoquinolinone:

To 84 ml of 47% aqueous hydrogen bromide was added 11.3 g of 3,4-dihydro-7-methoxy-2-(3-pyridylmethyl)-1 (2H)-isoquinolinone, and the mixture was refluxed under heating for 4.5 hours. After ice cooling, the mixture was neutralized with aqueous sodium hydroxide, made weakly acidic with acetic acid and shaken with ethyl acetate. The organic layer was washed with water and saturated brine in order, dried over anhydrous magnesium sulfate and concentrated in vacuo. The resultant residue was chromatographed on a column of silica gel, eluting with ethyl acetate to give 5.00 g of the titled compound.

mp. 136°–137° C.

c) Preparation of 7-(4-chlorophenoxy)-3,4-dihydro-2-(3-pyridylmethyl)-1 (2H)-isoquinolinone:

A mixture of 4.97 g of 3,4-dihydro-7-hydroxy-2-(3-pyridylmethyl)-1 (2H)-isoquinolinone, 4.50 g of 4-bromochlorobenzene, 3.88 g of cupric oxide, 5.39 g of potassium carbonate and 30 ml of pyridine was refluxed under heating for 20 hours. After finishing the reaction, the insoluble material was filtered, and the filtrate was concentrated in vacuo. The resultant residue was chromatographed on a column of silica gel, eluting with ethyl acetate to give 4.39 g of the titled compound.

mp. 93.5°–94.5° C.

The following compounds were prepared in the same manner as in Example 10 (1).

(2) 7-(4-nitrophenoxy)-3,4-dihydro-2-(3-pyridylmethyl)-1 (2H)-isoquinolinone (Compound No. 80 in Table)
mp. 155.5°–157.5° C.

(3) 7-(3-nitrophenoxy)-3,4-dihydro-2-(3-pyridylmethyl)-1 (2H)-isoquinolinone (Compound No. 81 in Table)
$^1$H NMR (CDCl$_3$) δ: 3.00 (t, 2H, J=7 Hz), 3.57 (t, 2H, J=7 Hz), 4.80 (s, 2H), 7.15–7.38 (m, 4H), 7.50 (t, 1H, J=8 Hz), 7.71–7.79 (m, 3H), 7.93–7.97 (m, 1H), 8.54–8.61 (m, 2H)

(4) 7-(2-nitrophenoxy)-3,4-dihydro-2-(3-pyridylmethyl)-1 (2H)-isoquinolinone (Compound No. 82 in Table)
$^1$H NMR (CDCl$_3$) δ: 2.96 (t, 2H, J=7 Hz), 3.53 (t, 2H, J=7 Hz), 4.77 (s, 2H), 7.06–7.28 (m, 5H), 7.51–7.59 (m, 1H), 7.70–7.72 (m, 2H), 7.96–7.99 (m, 1H), 8.54–8.59 (m, 2H)

(5) 7-phenoxy-3,4-dihydro-2-(3-pyridylmethyl)-1 (2H)-isoquinolinone (Compound No. 83 in Table)
$^1$H NMR (CDCl$_3$) δ: 2.93 (t, 2H, J=7 Hz), 3.51 (t, 2H, J=7 Hz), 4.77 (s, 2H), 6.99–7.39 (m, 8H), 7.71–7.78 (m, 2H), 8.55–8.60 (m, 2H)

(6) 7-(4-fluorophenoxy)-3,4-dihydro-2-(3-pyridylmethyl)-1 (2H)-isoquinolinone (Compound No. 85 in Table 1)
$^1$H NMR (CDCl$_3$) δ: 2.93 (t, 2H, J=7 Hz), 3.52 (t, 2H, J=7 Hz), 4.77 (s, 2H), 6.95–7.29 (m, 7H), 7.68–7.75 (m, 2H), 8.53–8.59 (m, 2H)

(7) 7-(4-methylphenoxy)-3,4-dihydro-2-(3-pyridylmethyl)-1 (2H)-isoquinolinone (Compound No. 86 in Table)
$^1$H NMR (CDCl$_3$) δ: 2.33 (s, 3H), 2.92 (t, 2H, J=7 Hz), 3.50 (t, 2H, J=7 Hz), 4.76 (s, 2H), 6.89–6.93 (m, 2H), 7.09–7.30 (m, 5H), 7.69–7.71 (m, 2H), 8.52–8.58 (m, 2H)

(8) 7-(4-cyanophenoxy)-3,4-dihydro-2-(3-pyridylmethyl)-1 (2H)-isoquinolinone (Compound No. 87 in Table)
mp. 102.5°–103.5° C.

(9) 7-(3-cyanophenoxy)-3,4-dihydro-2-(3-pyridylmethyl)-1 (2H)-isoquinolinone (Compound No. 88 in Table)
$^1$H NMR (CDCl$_3$) δ: 2.98 (t, 2H, J=6 Hz), 3.55 (t, 2H, J=6 Hz), 4.79 (s, 2H), 7.13–7.48 (m, 7H), 7.70–7.78 (m, 2H), 8.53–8.60 (m, 2H)

(10) 7-(2-cyanophenoxy)-3,4-dihydro-2-(3-pyridylmethyl)-1 (2H)-isoquinolinone (Compound No. 89 in Table)
mp. 120°–123° C.

(11) 7-(3,4-difluorophenoxy)-3,4-dihydro-2-(3-pyridylmethyl)-1 (2H)-isoquinolinone (Compound No. 90 in Table)

$^1$H NMR (CDCl$_3$) δ: 2.95 (t, 2H, J=7 Hz), 3.53 (t, 2H, J=7 Hz), 4.78 (s, 2H), 6.70–6.85 (m, 2H), 7.10–7.35 (m, 4H), 7.71–7.73 (m, 2H), 8.55–8.60 (m, 2H)

(12) 7-(3,4-dimethylphenoxy)-3,4-dihydro-2-(3-pyridylmethyl)-1 (2H)-isoquinolinone (Compound No. 91 in Table)

$^1$H NMR (CDCl$_3$) δ: 2.22 (s, 6H), 2.91 (t, 2H, J=6 Hz), 3.50 (t, 2H, J=6 Hz), 4.75 (s, 2H), 6.70–6.81 (m, 2H), 6.99–7.31 (m, 4H), 7.65–7.71 (m, 2H), 8.52–8.59 (m, 2H)

(13) 7-(4-methoxyphenoxy)-3,4-dihydro-2-(3-pyridylmethyl)-1 (2H)-isoquinolinone hydrochloride (Compound No. 92 in Table)

mp. 126°–132° C.

(14) 7-(4-acetylphenoxy)-3,4-dihydro-2-(3-pyridylmethyl)-1 (2H)-isoquinolinone (Compound No. 93 in Table)

$^1$H NMR (CDCl$_3$) δ: 2.57 (s, 3H), 2.96 (t, 2H, J=7 Hz), 3.53 (t, 2H, J=7 Hz), 4.77 (s, 2H), 6.96–7.00 (m, 2H), 7.11–7.30 (m, 3H), 7.68–7.95 (m, 4H), 8.50–8.59 (m, 2H)

(15) 7-(4-carbamoylphenoxy)-3,4-dihydro-2-(3-pyridylmethyl)-1 (2H)-isoquinolinone (Compound No. 94 in Table)

mp. 104°–107.5° C.

(16) 7-(4-chlorophenoxy)-3,4-dihydro-2-(3-pyridyl)-1 (2H)-isoquinolinone (Compound No. 121 in Table)

$^1$H NMR (CDCl$_3$) δ: 3.15 (t, 2H, J=6 Hz), 4.04 (t, 2H, J=6 Hz), 7.00–7.37 (m, 7H), 7.76–7.77 (m, 2H), 8.42–8.78 (m, 2H)

(17) 6-(3-nitrophenoxy)-3,4-dihydro-2-(3-pyridyl)-1 (2H)-isoquinolinone (Compound No. 124 in Table)

$^1$H NMR (CDCl$_3$) δ: 2.98 (t, 2H, J=7 Hz), 3.54 (t, 2H, J=7 Hz), 4.81 (s, 2H), 6.90–6.91 (m, 1H), 6.98–7.00 (m, 1H), 7.11–7.31 (m, 3H), 7.51 (t, 1H, J=8 Hz), 7.70–7.75 (m, 1H), 7.82–7.84 (m, 1H), 8.17 (d, 1H, J=8 Hz), 8.57–8.61 (m, 2H)

EXAMPLE 11

(1) Preparation of 2,3-dihydro-6-(4-fluorophenoxy)-2-(3-pyridylmethyl)-1H-isoindole-1-one (Compound No. 125 in Table)

a) Preparation of 2-hydroxymethyl-5-methoxy-N-(3-pyridylmethyl) benzamide:

A mixture of 919 mg of 6-methoxyisobenzofuran-1 (3H)-one and 1.82 g of 3-aminomethylpyridine was heated at 150° C. without solvent for 3 hours under stirring. After finishing the reaction, the mixture was chromatographed on a column of silica gel, eluting with ethyl acetate and then with tetrahydrofuran to give 1.40 g of the titled compound.

$^1$H NMR (CDCl$_3$) δ: 3.80 (s, 3H), 4.55 (s, 2H), 4.64 (d, 2H, J=6 Hz), 6.91–6.98 (m, 1H), 7.19–7.32 (m, 3H), 7.72–7.89 (m, 2H), 8.45–8.52 (m, 2H)

b) 2-acetoxymethyl-5-methoxy-N-(3-pyridylmethyl) benzamide

A solution of 710 mg of 2-hydroxymethyl-5-methoxy-N-(3-pyridylmethyl) benzamide and 317 mg of triethylamine in 10 ml of methylene chloride was chilled at 0° C., mixed with 320 mg of acetic anhydride and stirred at room temperature for 15 hours. The reaction mixture was washed with water and saturated brine in order. The organic layer was dried over anhydrous magnesium sulfate and concentrated in vacuo to give 820 mg of the titled compound.

$^1$H NMR (CDCl$_3$) δ: 1.97 (s, 3H), 3.82 (s, 3H), 4.64 (d, 2H, J=6 Hz), 5.18 (s, 2H), 6.93–6.98 (m, 1H), 7.05–7.08 (m, 2H), 7.27–7.37 (m, 2H).

c) Preparation of 2,3-dihydro-6-methoxy-2-(3-pyridylmethyl)-1H-isoindole-1-one:

To a suspension of 136 mg of sodium hydride (about 60%) in 7 ml of dimethylformamide chilled at 0° C. was added 820 mg of 2-acetoxymethyl-5-methoxy-N-(3-pyridylmethyl) benzamide and the resultant mixture was stirred at room temperature for 2 hours. The reaction mixture was mixed with water and shaken with toluene. The organic layer was washed with water, dried over anhydrous magnesium sulfate and concentrated in vacuo. The resultant residue was chromatographed on a column of silica gel, eluting with ethyl acetate to give 386 mg of the titled compound.

$^1$H NMR (CDCl$_3$) δ: 3.87 (s, 3H), 4.23 (s, 2H), 4.83 (s, 2H), 7.08–7.12 (m, 1H), 7.27–7.31 (m, 2H), 7.37–7.38 (m, 1H), 7.64–7.76 (m, 1H), 8.54–8.59 (m, 2H).

d) Preparation of 2,3-dihydro-6-hydroxy-2-(3-pyridylmethyl)-1H-isoindole-1-one:

The titled compound was prepared in the same manner as in Example 10 (1) b) by refluxing 2,3-dihydro-6-methoxy-2-(3-pyridylmethyl)-1H-isoindole-1-one in 47% hydrogen bromide under heating.

$^1$H NMR (DMSO$_{d6}$) δ: 4.27 (s, 2H), 4.74 (s, 2H), 6.97–7.08 (m, 2H), 7.24–7.41 (m, 2H), 7.50–7.53 (m, 1H), 8.51–8.57 (m, 2H), 9.81 (s, 1H).

e) Preparation of 2,3-dihydro-6-(4-fluorophenoxy)-2-(3-pyridylmethyl)-1H-isoindole-1-one:

The titled compound was prepared in the same manner as in Example 10 (1) c) from 2,3-dihydro-6-hydroxy-2-(3-pyridylmethyl)-1H-isoindole-1-once and 1-bromo-4-fluorobenzene.

mp. 115°–116° C.

The following compounds were prepared in the same manner as in Example 11 (1).

(2) 5-(4-chlorophenoxy)-2,3-dihydro-2-(3-pyridylmethyl)-1H-isoindole-1-one (Compound No. 126 in Table)

mp. 77°–82° C.

(3) 5-(4-chlorophenoxy)-2,3-dihydro-2-(4-pyridylmethyl)-1H-isoindole-1-one (Compound No. 127 in Table)

mp. 82°–87° C.

EXAMPLE 12

Preparation of 6-(4-chlorophenoxy)-3-(3-pyridylmethyl)-4 (3H)-quinazolinone (Compound No. 131 in Table)

a) Preparation of 6-bromo-3-(3-pyridylmethyl)-4 (3H)-quinazolinone:

A solution of 1.00 g of methyl 5-bromo-2-(N,N-dimethyl N′-formamidinyl) benzoate, 1.51 g of 3-aminomethylpyridine and 1.00 g of p-toluenesulfonic acid monohydrate in 45 ml of 1,4-dioxane was refluxed under heating for 3 hours. After finishing the reaction, the reaction mixture was mixed with water, made alkaline with 1N aqueous sodium hydroxide and extracted with methylene chloride. The organic layer was washed with water, dried over anhydrous magnesium sulfate and concentrated in vacuo to give 1.06 g of the titled compound.

mp. 161.5°–164.5° C.

b) Preparaiton of 6-(4-chlorophenoxy)-3-(3-pyridylmethyl)-4-(3H)-quinazolinone:

The titled compound was prepared in the same manner as in Example 1 (1) c) from 6-bromo-3-(3-pyridylmethyl)-4 (3H)-quinazolinone and 4-chlorophenol.
mp. 130°–133° C.

EXAMPLE 13

Preparation of 7-(4-chlorophenoxy)-2-(3-pyridylmethyl)-1 (2H)-phthalazinone (Compound No. 132 in Table)

a) Preparation of 7-bromo-2-(3-pyridylmethyl)-1 (2H)-phthalazinone:

The titled compound was prepared from 7-bromo-1 (2H)-phthalazinone and 3-chloromethylpyridine hydrochloride in the same manner as in Example 10 (1) a)

$^1$H NMR (CDCl$_3$) δ: 5.40 (s, 2H), 7.23–7.28 (m, 1H), 7.56 (d, 1H, J=8 Hz), 7.80–7.91 (m, 2H), 8.14 (s, 1H), 8.53–8.56 (m, 2H), 8.74 (broad s, 1H)

b) Preparation of 7-(4-chlorophenoxy)-2-(3-pyridylmethyl)-1 (2H)-phthalazinone:

The titled compound was prepared from 7-bromo-2-(3-pyridylmethyl)-1 (2H)-phthalazinone and 4-chlorophenol in the same manner as in Example 1 (1) c).
mp. 150°–151.5° C.

EXAMPLE 14

(1) Preparation of 7-(2-chlorobenzyloxy)-3,4-dihydro-2-(3-pyridylmethyl)-1 (2H)-isoquinolinone (Compound No. 98 in Table):

To a suspension of 32 mg of sodium hydride (about 60%) in 10 ml of dimethylformamide was added 100 mg of 3,4-dihydro-7-hydroxy-2-(3-pyridylmethyl)-1 (2H)-isoquinolinone, and the resultant mixture was stirred for 15 minutes. Then, 95 mg of 2-chloromethylchlorobenzene was added to the mixture, which was stirred at room temperature for 20 hours. After finishing the reaction, the mixture was mixed with water and shaken with ethyl acetate. The organic layer was dried over anhydrous magnesium sulfate and concentrated in vacuo. The resultant residue was chromatographed on a column of silica gel, eluting with ethyl acetate to give 144 mg of the titled compound.
mp. 88.5°–90° C.

The following compounds were prepared in the same manner as in Example 14 (1).

(2) 7-benzyloxy-3,4-dihydro-2-(3-pyridylmethyl)-1 (2H)-isoquinolinone (Compound No. 95 in Table)
$^1$H NMR (CDCl$_3$) δ: 2.89 (t, 2H, J=7 Hz), 3.49 (t, 2H, J=7 Hz), 4.79 (s, 2H), 5.12 (s, 2H), 7.01–7.42 (m, 8H), 7.69–7.76 (m, 2H), 8.53–8.60 (m, 2H)

(3) 7-(4-chlorobenzyloxy)-3,4-dihydro-2-(3-pyridylmethyl)-1 (2H)-isoquinolinone (Compound No. 96 in Table)
mp. 134.5°–136.5° C.

(4) 7-(3-chlorobenzyloxy)-3,4-dihydro-2-(3-pyridylmethyl)-1 (2H)-isoquinolinone (Compound No. 97 in Table)
$^1$H NMR (CDCl$_3$) δ: 2.90 (t, 2H, J=7 Hz), 3.52 (t, 2H, J=7 Hz), 4.80 (s, 2H) 5.10 (s, 2H), 7.02–7.11 (m, 2H), 7.26–7.31 (m, 4H), 7.45 (broad s, 1H), 7.70–7.73 (m, 2H), 8.54–8.60 (m, 2H)

(5) 7-(4-fluorobenzyloxy)-3,4-dihydro-2-(3-pyridylmethyl)-1 (2H)-isoquinolinone (Compound No. 99 in Table)
mp. 93°–94° C.

(6) 7-(2-fluorobenzyloxy)-3,4-dihydro-2-(3-pyridylmethyl)-1(2H)-isoquinolinone (Compound No. 100 in Table)
$^1$H NMR (CDCl$_3$) δ: 2.91 (t, 2H, J=6 Hz), 3.51 (t, 2H, J=6 Hz), 4.80 (s, 2H), 5.19 (s, 2H), 7.00–7.78 (m, 9H), 8.53–8.59 (m, 2H)

(7) 7-(2-bromobenzyloxy)-3,4-dihydro-2-(3-pyridylmethyl)-1 (2H)-isoquinolinone (Compound No. 101 in Table)
mp. 87°–89° C.

(8) 7-(4-nitrobenzyloxy)-3,4-dihydro-2-(3-pyridlmethyl)-1 (2H)-isoquinolinone (Compound No. 102 in Table)
mp. 140°–142° C.

(9) 7-(3-nitrobenzyloxy)-3,4-dihydro-(3-pyridylmethyl)-1 (2H)-isoquinolinone (Compound No. 103 in Table)
mp. 154.5°–156° C.

(10) 7-(2-nitrobenzyloxy)-3,4-dihydro-2-(3-pyridylmethyl)-1 (2H)-isoquinolinone (Compound No. 104 in Table)
mp. 130.5°–132° C.

(11) 7-(2-trifrifluoromethylbenzyloxy)-3,4-dihydro-2-(3-pyridylmethyl)-1 (2H)-isoquinolinone (Compound No. 105 in Table)
mp. 97.5°–98.5° C.

(12) 7-(2-methylbenzyloxy)-3,4-dihydro-2-(3-pyridylmethyl)-1 (2H)-isoquinolinone (Compound No. 106 in Table)
$^1$H NMR (CDCl$_3$) δ: 2.38 (s, 3H), 2.1 (t, 2H, J=7 Hz), 3.51 (t, 2H, J=7 Hz), 4.81 (s, 2H), 5.09 (s, 2H), 7.03–7.11 (m, 2H), 7.20–7.31 (m, 4H), 7.41–7.43 (m, 1H), 7.72–7.79 (m, 2H), 8.54–8.61 (m, 2H)

(13) 7-(2-ethylbenzyloxy)-3,4-dihydro-2-(3-pyridylmethyl)-1 (2H)-isoquinolinone (Compound No. 107 in Table)
$^1$H NMR (CDCl$_3$) δ: 1.26 (t, 3H, J=7 Hz), 2.72 (q, 2H, J=7 Hz), 2.91 (t, 2H, J=7 Hz), 3.50 (t, 2H, J=7 Hz), 4.81 (s, 2H), 5.11 (s, 2H), 7.00–7.78 (m, 9H), 8.52–8.61 (m, 2H)

(14) 7-(4-isopropylbenzyloxy)-3,4-dihydro-2-(3-pyridylmethyl)-1 (2H)-isoquinolinone (Compound No. 108 in Table)
$^1$H NMR (CDCl$_3$) δ: 1.26 (d, 6H, J=7 Hz), 2.87–3.00 (m, 2H+1H), 3.50 (t, 2H, J=7 Hz), 4.79 (s, 2H), 5.08 (s, 2H), 7.05–7.77 (m, 9H), 8.52–8.60 (m, 2H)

(15) 7-(2-isopropylbenzyloxy)-3,4-dihydro-2-(3-pyridylmethyl)-1 (2H)-isoquinolinone (Compound No. 109 in Table)
$^1$H NMR (CDCl$_3$) δ: 1.27 (d, 6H, J=7 Hz), 2.91 (t, 2H, J=6 Hz), 3.18 (sep, 1H, J=7 Hz), 3.52 (t, 2H, J=6 Hz), 4.81 (s, 2H), 5.12 (s, 2H), 7.01–7.80 (m, 9H), 8.54–8.61 (m; 2H)

(16) 7-(4-butylbenzyloxy)-3,4-dihydro-2-(3-pyridylmethyl)-1 (2H)-isoquinolinone (Compound No. 110 in Table)
$^1$H NMR (CDCl$_3$) δ: 0.93 (t, 3H, J=7 Hz), 1.23–1.64 (m, 4H), 2.60 (t, 2H, J=7 Hz), 2.91 (t, 2H, J=7 Hz), 3.50 (t, 2H, J=7 Hz), 4.80 (s, 2H), 5.08 (s, 2H), 7.06–7.76 (m, 9H), 8.57–8.60 (m, 2H)

(17) 7-(2,6-dimethylbenzyloxy)-3,4-dihydro-2-(3-pyridylmethyl)-1 (2H)-isoquinolinone (Compound No. 111 in Table)
$^1$H NMR (CDCl$_3$) δ: 2.39 (s, 6H), 2.92 (t, 2H, J=6 Hz), 3.53 (t, 2H, J=6 Hz), 4.82 (s, 2H), 5.11 (s, 2H), 7.02–7.33 (m, 6H), 7.72–7.75 (m, 1H), 7.82–7.83 (m, 1H), 8.55–8.62 (m, 2H)

(18) 7-(2-methoxybenzyloxy)-3,4-dihydro-2-(3-pyridylmethyl)-1 (2H)-isoquinolinone (Compound No. 112 in Table)

$^1$H NMR (CDCl$_3$) δ: 2.90 (t, 2H, J=7 Hz), 3.50 (t, 2H, J=7 Hz, 3.87 (s, 3H), 4.80 (s, 2H), 5.17 (s, 2H), 6.90-7.01 (m, 2H), 7.08 (broad s, 2H), 7.26-7.37 (m, 2H), 7.47 (d, 1H, J=7 Hz), 7.72-7.80 (m, 2H), 8.54-8.61 (m, 2H)

(19) 7-(2-cyanobenzyloxy)-3,4-dihydro-2-(3-pyridylmethyl)-1 (2H)-isoquinolinone (Compound No. 113 in Table)

$^1$H NMR (CDCl$_3$) δ: 2.92 (t, 2H, J=7 Hz), 3.51 (t, 2H, J=7 Hz), 4.80 (s, 2H), 5.30 (s, 2H), 7.05-7.47 (m, 4H), 7.60-7.78 (m, 5H), 8.54-8.60 (m, 2H)

(20) 7-(2-methoxycarbonylbenzyloxy)-3,1-dihydro-2-(3-pyridylmethyl)-1 (2H)-isoquinolinone (Compound No. 115 in Table)

$^1$H NMR (CDCl$_3$) δ: 2.90 (t, 2H, J=7 Hz), 3.50 (t, 2H, J=7 Hz), 3.90 (s, 3H), 4.79 (s, 2H), 5.54 (s, 2H), 7.09-7.76 (m, 8H), 8.02 (d, 1H, J=8 Hz), 8.54-8.60 (m, 2H)

(21) 7-(2-methoxycarbonylbenzyloxy)-3,4-dihydro-2-(2-pyridylmethyl)-1 (2H)-isoquinolinone (Compound No. 116 in Table)

$^1$H NMR (CDCl$_3$) δ: 2.92 (t, 2H, J=7 Hz), 3.63 (t, 2H, J=7 Hz), 3.89 (s, 3H), 4.90 (s, 2H), 5.53 (s, 2H), 7.02-7.76 (m, 9H), 8.01 (d, 1H, J=8 Hz), 8.53-8.55 (m, 1H)

(22) 7-(2-methoxycarbonylbenzyloxy)-3,4-dihydro-2-(4-pyridylmethyl)-1 (2H)-isoquinolinone (Compound No. 117 in Table)

mp. 78°-79° C.

(23) 7-[2-(N,N-dimethylcarbamoyl) benzyloxy]-3,4-dihydro-2-(3-pyridylmethyl)-1 (2H)-isoquinolinone (Compound No. 118 in Table)

$^1$H NMR (CDCl$_3$) δ: 2.86-2.90 (m, 3H+2H), 3.09 (s, 3H), 3.49 (t, 2H, J=6 Hz), 4.79 (s, 2H), 5.13 (s, 2H), 7.00-7.13 (m, 2H), 7.23-7.42 (m, 4H), 7.51-7.57 (m, 1H), 7.68-7.72 (m, 2H), 8.53-8.59 (m, 2H)

(24) 7-(2-methylsulfonylbenzyloxy)-3,4-dihydro-2-(3-pyridylmethyl)-1 (2H)-isoquinolinone (Compound No. 119 in Table)

mp. 121.5°-123° c.

(25) 7-benzyloxy-3,4-dihydro-2-[1-(3-pyridyl) ethyl]-1 (2H)-isoquinolinone (Compound No. 120 in Table)

$^1$H NMR (CDCl$_3$) δ: 1.61-1.65 (m, 3H), 2.76-2.81 (m, 2H), 3.06-3.15 (m, 2H), 3.37-3.48 (m, 2H), 5.12 (broad s, 2H), 6.27 (broad q, 1H, J=7 Hz), 7.06 (broad s, 2H), 7.25-7.47 (m, 6H), 7.70-7.77 (m, 2H), 8.54-8.66 (m, 2H)

(26) 6-(2-nitrobenzyloxy)-3,4-dihydro-2-(3-pyridylmethyl)-1 (2H)-isoquinolinone (Compound No. 123 in Table)

mp. 101°-103° C.

(27) 7-(2-nitrobenzyloxy)-3,4-dihydro-2-(5-pyridylmethyl)-1 (2H)-isoquinolinone (Compound No. 122 in Table)

mp. 161°-162° C.

(28) 4-(4-chlorobenzyloxy)-2-(3-pyridylmethyl)-1H-isoindole-1,3-(2H)-dione (Compound No. 75 in Table)

mp. 167°-169° C.

EXAMPLE 15

(1) Preparation of 7-(4-chlorophenoxy)-2-(3-pyridylmethyl)-1 (2H)-isoquinolinone (Compound No. 128 in Table)

a) Preparation of 7-(4-chlorophenoxy) isocoumarin:

A solution of 500 mg of 7-(4-chlorophenoxy)-3,4-dihydroisocoumarin, 325 mg of N-bromosuccinimide and 20 mg of benzoyl peroxide in 20 ml of carbon tetrachloride was refluxed under heating for 2 hours. After finishing the reaction, the mixture was washed with water, dried over anhydrous magnesium sulfate and concentrated in vacuo. The resultant residue was mixed with 10 ml of toluene and 490 mg of 1,8-diazabicyclo [5, 4, 0] undec-7-ene and stirred at room temperature for 1 hour. The toluene was evaporated in vacuo, and the resultant residue was chromatographed on a column of silica gel, eluting with ethyl acetate and hexane (1:1) to give 367 mg of the titled compound.

mp 76.5°-77° C.

b) Preparation of 7-(4-chlorophenoxy)-2-(3-pyridylmethyl)-1 (2H)-isoquinolinone:

A mixture of 100 mg of 7-(4-chlorophenoxy) isocoumarin and 377 mg of 3-aminomethylpyridine was heated at 180° C. without solvent under stirring for 5 hours. After finishing the reaction, the mixture was chromatographed on a column of silica gel, eluting with ethyl acetate to give 97 mg of the titled compound.

mp. 115.5°-116.5° C.

The following compounds were prepared in the same manner as in Example 15 (1).

(2) 7-(4-methylphenoxy)-2-(3-pyridylmethyl)-1 (2H)-isoquinolinone (Compound No. 129 in Table)

$^1$H NMR (CDCl$_3$) δ: 2.32 (s, 3H), 5.15 (s, 2H), 6.47 (d, 1H, J=7 Hz), 6.93-7.48 (m, 8H), 7.64-7.67 (m, 1H), 7.88-7.89 (m, 1H), 8.50-8.51 (m, 1H), 8.61 (broad s, 1H)

(3) 7-(4-chlorophenoxy)-2-(3-pyridyl)-1 (2H)-isoquinolinone (Compound No. 130 in Table)

mp. 130°-131° C.

EXAMPLE 16

(1) Preparation of 3-[[5-[N,N-bis (4-cyanophenyl) amino]-1,3-dioxo-1,2H-isoindole-2-yl]methyl]pyridine 1-oxide (Compound No. 70 in Table)

To a solution of 1 g of 5-[N,N-bis (4-cycanophenyl) amino]-2-(3-pyridylmethyl)-1H-isoindole-1,3 (2H)-dione in 200 ml of chloroform was added 470 mg of m-chloroperbenzoic acid, and the resultant mixture was stirred at room temperature for 15 hours. This solution was washed with dilute aqueous sodium hydroxide, dried over anhydrous sodium sulfate and chromatographed on a column of silica gel eluting with chloroform and methanol (100:1) to give 0.95 g of the titled compound.

mp. 259°-262° C.

The following compound was prepared in the same manner as in Example 16 (1).

(2) 3-[[5-[N,N-bis (4-chlorophenyl) amino]-1,3-dioxo-1,2H-isoindole-2-yl]methyl]pyridine 1-oxide (Compound No. 71 in Table)

mp. 130°-133° C.

EXAMPLE 17

Preparation of Tablet

To 1000 g of sufficiently pulverized 5-[N,N-bis (4-chlorophenyl) amino]-2-(3-pyridylmethyl)-1H-isoindole-1,3 (2H)-dione (Compound No. 60 in Table) were added 5900 g of lactose, 2000 g of crystalline cellulose, 1000 g of low substitution degree of hydroxypropyl cellulose and 100 g of magnesium stearate, and the resultant mixture was mixed well and subjected to a tableting machine to give naked tablets which contain 10 mg of said compound per tablet weighing 100 mg by direct punching method. The naked tablets were coated with sugar or film coat to give sugar coating tablets and film coating tablets.

EXAMPLE 18

Preparation of Capsule

To 1000 g of sufficiently pulverized 5-[N,N-bis (4-cyanophenyl) amino]-2-(3-pyridylmethyl)-1H-isoindole-1,3 (2H)-dione (Compound No. 63 in Table) were added 3000 g of corn starch, 6900 g of lactose, 1000 g of crystalline cellulose and 100 g of magnesium stearate, and the resultant mixture was encapsuled, to give capsules which contain 10 mg of said compound per capsule weighing 120 mg.

EXAMPLE 19

Preparation of Inhalant

A mixture of 5 g of sufficiently pulverized 5-(4-chlorophenoxy)-2-(3-pyridylmethyl)-1H-isoindole-1, 3 (2H)-dione (Compound No. 25 in Table), 10 g of middle chained saturated fatty acid triglyceride and 0.2 g of sorbitan monooleate was stirred well, and 15.2 mg of the admixture was charged in a 5 ml volume of aluminum vessel for aerosol. Further, 84.8 mg of Freon 12/114 (1:1 mixture) was charged in the vessel at low temperature, and the vessel was equipped with a quantitative adaptor of 10.0 µl per jet to give an inhalant of quantitative spray containing 5 mg of said compound in one vessel of 5 ml volume.

Pharmacological data showing effectiveness of the compounds of the present invention are shown below.

Compound WEB 2086 in Tables 10, 11 and 12, which is described in Japanese Patent Publication (Kokai) Sho 61-176591 as a PAF antagonist has the following structure.

WEB 2086

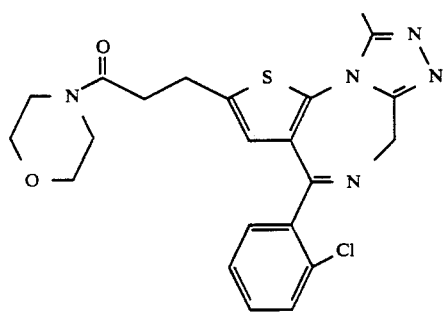

EXPERIMENT 1

Rabbit Platelet Aggregation Inhibitory Activity

To 0.9 volume of blood collected from jugular vein of a New Zealand white male rabbit weighing from 2.5 to 3.5 kg was added 0.1 volume of 3.8% aqueous sodium citrate, and the mixture was centrifuged at 110 xg for 15 minutes to give PRP (poly platelet plasma). Assay of platelet aggregation induced by PAF was effected using 4 channels aggregometer (Manufacturer: Nicoh Bioscience Co.) according to Bohn et al, Turbimetry [J. Physiology, Vol. 168, p.178, 1963]. Table 11 shows $IC_{50}$ (a concentration of test compound necessary to inhibit 50% of platelet aggregation) of test compounds. The final concentration of PAF in the reaction mixture was adjusted to $10^{-10}$M.

TABLE 11

| Compound No. | Rabbit Platelet Aggregation Inhibitory activity $IC_{50}$ (M) |
|---|---|
| 2 | $2.6 \times 10^{-8}$ |
| 25 | $1.0 \times 10^{-8}$ |
| 45 | $1.9 \times 10^{-8}$ |
| 50 | $2.4 \times 10^{-8}$ |
| 60 | $2.6 \times 10^{-9}$ |
| 63 | $1.7 \times 10^{-9}$ |
| 68 | $1.8 \times 10^{-9}$ |
| 72 | $3.2 \times 10^{-8}$ |
| 84 | $1.0 \times 10^{-8}$ |
| 125 | $3.6 \times 10^{-8}$ |
| 128 | $1.8 \times 10^{-8}$ |
| 131 | $3.1 \times 10^{-8}$ |
| WEB2086 | $4.0 \times 10^{-8}$ |

EXPERIMENT 2

Activity to Mouse Death due to Shock induced by PAF

Test was effected according to Young et al. method, Prostaglandins, Vol. 30, p.545, 1985. Lethal test was effected by treating starved male ICR mouse weighing from 25 g to 30 g with PAF without anesthesia. Test Compound was orally administered 1 hour prior to tail intravenous administration of 100 µg/kg of PAF. Survival rate of the test animal was examined 24 hours after intravenous administration of PAF. Table 12 shows $ED_{50}$ (a dosage of test compound necessary to inhibit 50% death due to PAF) of test compounds.

TABLE 12

| Compound No. | Activity to death due to shock induced by PAF. $ED_{50}$ (mg/kg) |
|---|---|
| 2 | 2.1 |
| 25 | 1.3 |
| 45 | 0.6 |
| 50 | 0.32 |
| 60 | 0.019 |
| 63 | 0.007 |
| 72 | 0.4 |
| 130 | 0.018 |
| WEB2086 | 1.0 |

EXPERIMENT 3

Activity to Contraction of the Respiratory Tract of Guinea Pig due to PAF

Hartley male guinea pigs weighing from 350 g to 500 g were anesthetized by intraperitoneal administration of 50 mg/kg of sodium pentobarbital. Contraction of the respiratory tract was measured by inserting a cannula into trachea and measuring under artificial ventilation according to Conzet et al, Arch. Exp. Pharmacol. Vol. 195, p. 71. Test compound was orally administered 1 hour prior to intravenous administration of 0.3 µg/kg of PAF. Table 13 shows $ED_{50}$ (volume of test compound necessary to inhibit 50% contraction of the respiratory tract due to PAF) of test compounds.

TABLE 13

| Compound No. | Activity to Contraction of the Respiratory Tract of Guinea Pig due to PAF ED$_{50}$ (mg/kg) |
|---|---|
| 2 | 0.15 |
| 25 | 0.14 |
| 60 | 0.019 |
| 63 | 0.006 |
| WEB2086 | 0.15 |

As clearly shown in various pharmacological data above, the compounds of the present invention exhibit potent PAF antagonism.

Based on the above fact, the compounds of the present invention are found useful as PAF antagonists and effective for therapy and prophylaxis of diseases caused by PAF. Illustrative diseases include bronchial asthma, nephritis, shocks (e.g. anaphylaxy shock, endotoxin shock, bleeding shock, etc.), cardiac infarction, cerebral hemorrhage (e.g. cerebral hemorrhage, cerebral thrombosis), ulcer (e.g. gastric ulcer, etc.), DIC (disseminated intravascular coagulation), autoimmune diseases (e.g. rheumatism, etc.), thrombosis, and the like.

EXPERIMENT 4

Acute Toxicity

To groups of male and female SD (CD) rat of five week age, each group consisting of 3 rats, was orally administered a suspension of 0.5% aqueous CMC-Na (sodium carboxy methyl cellulose) solution, and symptoms of the animal were observed for 14 days. The number of the dead animal was counted and shown in Table 14.

TABLE 14

| Compound No. | Acute Toxicity (LD$_{50}$ mg/kg) |
|---|---|
| 2 | >2000 |
| 25 | >2000 |
| 60 | >2000 |
| 63 | >2000 |

Effect of the Invention

The compounds of the present invention show excellent PAF antagonism and are effective for therapy and prophylaxis of diseases caused by PAF (e.g. bronchial asthma, nephritis, shocks, cardiac infarction, cerebral hemorrhage, ulcer, DIC, autoimmune disease, thrombosis, etc.)

What is claimed is:

1. A benzamide derivative of the following formula (I):

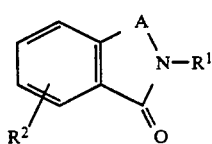

wherein:

R$^1$ represents a group of the following formula (II)

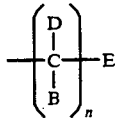

(in the above formula (II), n represents an integer from 0 to 2, B and D each independently represent hydrogen atom or C$_1$-C$_4$ alkyl group, E represents a heterocyclic group selected from the group consisting of thienyl, furyl, imidazolyl, pyrazolyl, pyridyl, N-oxypyridyl, and pyrimidyl groups, which is unsubstituted or substituted by a C$_1$-C$_4$ alkyl group or a C$_1$-C$_4$ alkyoxy group), R$^2$ represents C$_6$-C$_{12}$ aryl group, C$_6$-C$_{12}$ aryloxy group, C$_6$-C$_{12}$ arylthio group, benzyloxy group or C$_7$-C$_{13}$ arylcarbonyl group, which is unsubstituted or substituted, or a group of the following formula (III):

(in the above formula (III), R$^3$ represents C$_6$-C$_{12}$ aryl group which is unsubstituted or substituted and R$^4$ represents C$_6$-C$_{12}$ aryl group which is unsubstituted or substituted, hydrogen atom, C$_1$-C$_4$ alkyl group or C$_3$-C$_8$ cycloalkyl group) or a group of the following formula (IV):

(in the above formula (IV), R$^5$ represents C$_6$-C$_{12}$ aryl group which is unsubstituted or substituted, and R$^6$ represents C$_6$-C$_{12}$ aryl group which is unsubstituted or substituted, hydrogen atom, C$_1$-C$_4$ alkyl group or C$_3$-C$_8$ cycloalkyl group), and A represents —N=N— and optical antipodes thereof or pharmacologically acceptable salts thereof.

2. The compound according to claim 1, wherein R$^1$ represents a group of the formula (II), n represents 1, B and D each represents hydrogen atom, and E represents pyridyl group or N-oxypyridyl group.

3. The compound according to claim 2, wherein R$^2$ represents aryloxy group which is unsubstituted or substituted or a group of the following formula (III):

wherein R$^3$ and R$^4$ are as defined above.

4. The compound according to claim 1, wherein the substituent which may be present on the aryl group, the aryloxy group, the arylthio group, and benzyloxy group or the arylcarbonyl group represents by R$^2$ and the substituent which may present on aryl group represented by R$^3$, R$^4$, R$^5$ and R$^6$ are one or more groups selected from the group consisting of C$_1$-C$_4$ alkyl group, C$_3$-C$_8$ cycloalkyl, C$_1$-C$_4$ alkoxy group, C$_2$-C$_4$ alkenyl group, C$_2$-C$_4$ alkynyl group, C$_3$-C$_4$ alkenyloxy group, C$_3$-C$_4$ alkynyloxy group, hydroxyl group, halogen atom, amino group, C$_1$-C$_4$ alkynylamino group, C$_2$-C$_6$ dialkylamino group, trifluoromethyl group, cyano group, nitro group, C$_1$-C$_4$ hydroxyalkyl group, C$_1$-C$_4$ aminoalkyl group, C$_1$-C$_4$ cyanoalkyl group, —COOR$^7$, —COR$^7$, —SO$_2$R$^7$, —NHCOOR$^7$, NR$^8$COR$^9$, CONR$^8$R$^{10}$, —OCONR$^8$R$^9$, NR$^8$CONR$^9$R$^{10}$ and —CONR$^8$CR$^9$ (in which R$^7$ and $R^9$ each independently represent $C_1$-$C_4$ alkyl group or $C_3$-$C_8$ cycloalkyl group, and $R^8$ and $R^{10}$ each independently represent hydrogen atom, $C_1$-$C_4$ alkyl group or $C_3$-$C_8$ cycloalkyl group).

5. The compound according to claim 4 wherein the substituent which may present on the aryl group, the aryloxy group, the arylthio group, the benzyloxy group or the arylcarbonyl group represented by $R^2$ and the substituent which may present on aryl group represented by $R^3$, $R^4$, $R^5$ and $R^6$ are one or more groups selected from the group consisting of $C_1$-$C_4$ alkyl group, $C_1$-$C_4$ alkoxy group, $C_3$-$C_4$ alkynyloxy group, hydroxyl group, halogen atom, trifluoromethyl group, cyano group, nitro group, $C_1$-$C_4$ hydroxyalkyl group, —$COOR^7$, —$COR^7$, —$SO_2R^7$ and —$CONR^8R^{10}$ (in which $R^7$ represents $C_1$-$C_4$ alkyl group, and $R^8$ and $R^{10}$ each independently represent hydrogen atom or $C_1$-$C_4$ alkyl group).

6. The compound according to claim 1, wherein n represents 1, B and D represent hydrogen atom, E represents pyridyl group and $R^2$ represents a group of the following formula (III):

$$R^3R^4N \qquad (III)$$

wherein $R^3$ and $R^4$ represent 4-cyanophenyl group.

7. A pharmaceutical composition a compound according to claim 1 and a pharmaceutically acceptable carrier.

8. A prophylactic or therapeutic pharmaceutical composition for diseases caused by platelet activating factor, which comprises a compound according to claim 1 as an active ingredient.

* * * * *